(12) United States Patent
Wang

(10) Patent No.: US 10,675,386 B2
(45) Date of Patent: *Jun. 9, 2020

(54) DRUG COATED BALLOON CATHETERS FOR NONVASCULAR STRICTURES

(71) Applicant: Urotronic, Inc., Plymouth, MN (US)

(72) Inventor: Lixiao Wang, Henderson, NV (US)

(73) Assignee: Urotronic, Inc., Plymouth, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/267,434

(22) Filed: Feb. 5, 2019

(65) Prior Publication Data

US 2019/0167854 A1  Jun. 6, 2019

Related U.S. Application Data

(63) Continuation of application No. 14/438,327, filed as application No. PCT/US2013/064842 on Oct. 14, 2013.

(60) Provisional application No. 61/795,790, filed on Oct. 26, 2012.

(51) Int. Cl.
*A61L 29/16* (2006.01)
*A61L 29/08* (2006.01)

(52) U.S. Cl.
CPC ............ *A61L 29/16* (2013.01); *A61L 29/08* (2013.01); *A61L 29/085* (2013.01); *A61L 2300/41* (2013.01); *A61L 2300/416* (2013.01); *A61L 2300/45* (2013.01); *A61L 2300/602* (2013.01); *A61L 2300/606* (2013.01); *A61L 2300/802* (2013.01); *A61L 2420/06* (2013.01)

(58) Field of Classification Search
None
See application file for complete search history.

(56) References Cited

U.S. PATENT DOCUMENTS

| 5,171,299 A | 12/1992 | Heitzmann et al. |
| 5,263,931 A | 11/1993 | Miller |
| 5,312,430 A | 5/1994 | Rosenbluth et al. |

(Continued)

FOREIGN PATENT DOCUMENTS

| CN | 101610798 A | 12/2009 |
| CN | 104936629 A | 9/2015 |

(Continued)

OTHER PUBLICATIONS

"Stricture" definition accessed online on Jun. 10, 2019 at www.merriam-webster.com/dictionary/stricture. (Year: 2019).*

(Continued)

*Primary Examiner* — Carlos A Azpuru
*Assistant Examiner* — Casey S Hagopian
(74) *Attorney, Agent, or Firm* — Schwegman Lundberg & Woessner, P.A.

(57) ABSTRACT

Embodiments of the present invention provide a method for treatment of nonvascular body lumen strictures such as benign prostatic hyperplasia (BPH), urethral strictures, ureteral strictures, prostate cancer, esophageal strictures, sinus strictures, biliary tract strictures, asthma and chronic obstructive pulmonary disease (COPD). The method involves delivering, preferably via drug coated balloon catheters, of anti-inflammatory and anti-proliferative drugs (rapamycin or paclitaxel and their analogues) and one or more additives.

21 Claims, 2 Drawing Sheets

(56) References Cited

U.S. PATENT DOCUMENTS

| | | | |
|---|---|---|---|
| 5,314,443 A | 5/1994 | Rudnick | |
| 5,419,763 A | 5/1995 | Hildebrand | |
| 5,423,755 A | 6/1995 | Kesten et al. | |
| 5,718,684 A | 2/1998 | Gupta | |
| 5,752,522 A | 5/1998 | Murphy | |
| 5,904,648 A | 5/1999 | Arndt et al. | |
| 6,059,713 A | 5/2000 | Urick et al. | |
| 6,268,390 B1 | 7/2001 | Kunz | |
| 6,306,421 B1 | 10/2001 | Kunz et al. | |
| 6,403,635 B1 | 6/2002 | Kinsella et al. | |
| 6,495,579 B1 | 12/2002 | Hunter | |
| 6,515,009 B1 | 2/2003 | Kunz et al. | |
| 6,530,948 B1 | 3/2003 | Vrba | |
| 6,663,881 B2 | 12/2003 | Kunz et al. | |
| 6,730,064 B2 | 5/2004 | Ragheb et al. | |
| 7,803,149 B2 | 9/2010 | Bates et al. | |
| 7,811,622 B2 | 10/2010 | Bates et al. | |
| 7,882,841 B2 | 2/2011 | Aljuri et al. | |
| 8,052,668 B2 | 11/2011 | Sih | |
| 8,092,864 B2 | 1/2012 | Isch et al. | |
| 8,241,249 B2 | 8/2012 | Wang | |
| 8,244,344 B2 | 8/2012 | Wang | |
| 8,257,305 B2 | 9/2012 | Speck et al. | |
| 8,366,660 B2 | 2/2013 | Wang | |
| 8,366,662 B2 | 2/2013 | Wang | |
| 8,403,910 B2 | 3/2013 | Wang | |
| 8,404,300 B2 | 3/2013 | Wang | |
| 8,414,525 B2 | 4/2013 | Wang | |
| 8,414,526 B2 | 4/2013 | Wang | |
| 8,414,909 B2 | 4/2013 | Wang | |
| 8,414,910 B2 | 4/2013 | Wang | |
| 8,425,459 B2 | 4/2013 | Wang | |
| 8,430,055 B2 | 4/2013 | Wang et al. | |
| 8,439,868 B2 | 5/2013 | Speck et al. | |
| 8,557,272 B2 | 10/2013 | Zhao | |
| 8,586,125 B2 | 11/2013 | Hossainy et al. | |
| 8,673,387 B2 | 3/2014 | Bates et al. | |
| 8,722,132 B2 | 5/2014 | Labrecque et al. | |
| 9,066,990 B2 | 6/2015 | Speck et al. | |
| 9,242,081 B2 | 1/2016 | Drasler et al. | |
| 10,245,419 B2 | 4/2019 | Drasler et al. | |
| 2003/0203991 A1 | 10/2003 | Schottman et al. | |
| 2004/0098019 A1 | 5/2004 | Tomaschko et al. | |
| 2004/0144387 A1 | 7/2004 | Amar | |
| 2004/0267355 A1 | 12/2004 | Scott et al. | |
| 2005/0054978 A1 | 3/2005 | Segal et al. | |
| 2005/0196518 A1 | 9/2005 | Stenzel | |
| 2005/0249770 A1 | 11/2005 | Hunter | |
| 2006/0083768 A1 | 4/2006 | Labrecque et al. | |
| 2007/0005094 A1* | 1/2007 | Eaton | A61B 17/24 606/199 |
| 2007/0009692 A1 | 1/2007 | Wang et al. | |
| 2007/0027523 A1 | 2/2007 | Toner et al. | |
| 2007/0088255 A1 | 4/2007 | Toner et al. | |
| 2008/0025952 A1 | 1/2008 | Scheule et al. | |
| 2008/0113035 A1 | 5/2008 | Hunter | |
| 2008/0118544 A1* | 5/2008 | Wang | A61K 31/337 424/423 |
| 2008/0175887 A1* | 7/2008 | Wang | A61K 31/337 424/434 |
| 2008/0245375 A1 | 10/2008 | Trudel | |
| 2008/0255508 A1 | 10/2008 | Wang | |
| 2008/0255509 A1 | 10/2008 | Wang | |
| 2008/0255510 A1 | 10/2008 | Wang | |
| 2008/0276935 A1 | 11/2008 | Wang | |
| 2009/0018565 A1 | 1/2009 | To et al. | |
| 2009/0028920 A1 | 1/2009 | Hodges | |
| 2009/0171241 A1 | 7/2009 | Garcia et al. | |
| 2009/0283206 A1 | 11/2009 | Eskaros et al. | |
| 2010/0015200 A1* | 1/2010 | McClain | A61L 17/005 424/423 |
| 2010/0030183 A1 | 2/2010 | Toner et al. | |
| 2010/0049182 A1 | 2/2010 | Ryan et al. | |
| 2010/0055294 A1 | 3/2010 | Wang et al. | |
| 2010/0198150 A1 | 8/2010 | Michal et al. | |
| 2010/0209472 A1 | 8/2010 | Wang | |
| 2010/0233228 A1 | 9/2010 | Speck | |
| 2010/0285085 A1 | 11/2010 | Stankus et al. | |
| 2011/0008260 A1 | 1/2011 | Flanagan | |
| 2011/0015664 A1 | 1/2011 | Kangas et al. | |
| 2011/0098683 A1 | 4/2011 | Wiita et al. | |
| 2011/0144578 A1 | 6/2011 | Pacetti et al. | |
| 2011/0159169 A1 | 6/2011 | Wang | |
| 2011/0160575 A1 | 6/2011 | Beyar et al. | |
| 2011/0160658 A1 | 6/2011 | Wang | |
| 2011/0160660 A1 | 6/2011 | Wang | |
| 2011/0166548 A1 | 7/2011 | Wang | |
| 2011/0196340 A1 | 8/2011 | Barry et al. | |
| 2011/0295200 A1 | 12/2011 | Speck et al. | |
| 2011/0300221 A1 | 12/2011 | Kunz et al. | |
| 2012/0029426 A1 | 2/2012 | Wang | |
| 2012/0035530 A1 | 2/2012 | Wang | |
| 2012/0109105 A1 | 5/2012 | Cambronne | |
| 2012/0172796 A1 | 7/2012 | Chappa | |
| 2012/0231037 A1 | 9/2012 | Levi et al. | |
| 2012/0239001 A1 | 9/2012 | Barry et al. | |
| 2012/0296274 A1 | 11/2012 | Slager | |
| 2012/0302954 A1 | 11/2012 | Zhao | |
| 2012/0316633 A1 | 12/2012 | Flanagan et al. | |
| 2013/0197434 A1 | 8/2013 | Wang | |
| 2013/0231638 A1 | 9/2013 | Speck et al. | |
| 2013/0245058 A1 | 9/2013 | Hoffmann et al. | |
| 2013/0253466 A1 | 9/2013 | Campbell et al. | |
| 2013/0253475 A1 | 9/2013 | Wang | |
| 2013/0261603 A1 | 10/2013 | Wang | |
| 2013/0304029 A1 | 11/2013 | Barry et al. | |
| 2014/0005541 A1 | 1/2014 | Bates et al. | |
| 2014/0228751 A1 | 8/2014 | Speck et al. | |
| 2014/0228752 A1 | 8/2014 | Speck et al. | |
| 2014/0378896 A1 | 12/2014 | Venturelli | |
| 2015/0231375 A1 | 8/2015 | Kubo et al. | |
| 2015/0273117 A1 | 10/2015 | Wang | |
| 2016/0082159 A1 | 3/2016 | Orlowski | |
| 2016/0338793 A1 | 11/2016 | Shohat et al. | |
| 2017/0028105 A1 | 2/2017 | Ahlering et al. | |
| 2017/0086929 A1 | 3/2017 | Moll et al. | |
| 2018/0104383 A1 | 4/2018 | Wang et al. | |
| 2019/0015639 A1 | 1/2019 | Wang et al. | |
| 2019/0015640 A1 | 1/2019 | Wang et al. | |
| 2019/0344053 A1 | 11/2019 | Wang et al. | |
| 2019/0374685 A1 | 12/2019 | Wang et al. | |

FOREIGN PATENT DOCUMENTS

| | | |
|---|---|---|
| CN | 107635593 A | 1/2018 |
| EP | 0474906 A1 | 3/1992 |
| EP | 1135165 A1 | 9/2001 |
| EP | 1143968 B1 | 8/2003 |
| EP | 1539266 B1 | 4/2008 |
| EP | 2292225 B1 | 5/2012 |
| EP | 2098230 B1 | 6/2012 |
| EP | 2262547 B1 | 1/2013 |
| EP | 2324866 B1 | 6/2014 |
| EP | 2324867 B1 | 6/2014 |
| EP | 2531229 B1 | 12/2014 |
| EP | 2451496 B1 | 7/2015 |
| EP | 2911711 | 9/2015 |
| JP | 2010540159 A | 12/2010 |
| JP | 2014523790 A | 9/2014 |
| JP | 2015536709 A | 12/2015 |
| JP | 2018517454 A | 7/2018 |
| WO | WO-9728840 A1 | 8/1997 |
| WO | 0025848 | 5/2000 |
| WO | WO-0032238 | 6/2000 |
| WO | WO-2011147407 A2 | 12/2001 |
| WO | WO-2009051614 A1 | 4/2009 |
| WO | WO-2011008393 A2 | 1/2011 |
| WO | WO-2011119159 A1 | 9/2011 |
| WO | WO-2012122023 A2 | 9/2012 |
| WO | WO-2013015941 A1 | 1/2013 |
| WO | WO-2014066085 A1 | 5/2014 |
| WO | WO-2016073294 A1 | 5/2016 |
| WO | WO-2016172343 A1 | 10/2016 |
| WO | WO-2018204782 A1 | 11/2018 |

(56) References Cited

FOREIGN PATENT DOCUMENTS

OTHER PUBLICATIONS

"U.S. Appl. No. 14/438,327, Advisory Action dated Jul. 18, 2018", 6 pgs.
"U.S. Appl. No. 14/438,327, Final Office Action dated Apr. 2, 2018", 14 pgs.
"U.S. Appl. No. 14/438,327, Final Office Action dated May 3, 2017", 10 pgs.
"U.S. Appl. No. 14/438,327, Non Final Office Action dated Jan. 28, 2019", 14 pgs.
"U.S. Appl. No. 14/438,327, Non Final Office Action dated Sep. 29, 2017", 11 pgs.
"U.S. Appl. No. 14/438,327, Non Final Office Action dated Oct. 6, 2016", 10 pgs.
"U.S. Appl. No. 14/438,327, Preliminary Amendment filed Jul. 28, 2015", 9 pgs.
"U.S. Appl. No. 14/438,327, Response filed Jun. 1, 2018 to Final Office Action dated Apr. 2, 2018", 16 pgs.
"U.S. Appl. No. 14/438,327, Response filed Jul. 27, 2017 to Final Office Action dated May 3, 2017", 13 pgs.
"U.S. Appl. No. 14/438,327, Response filed Aug. 1, 2018 to Advisory Action dated Jul. 18, 2018 and Final Office Action dated Apr. 2, 2018", 17 pgs.
"U.S. Appl. No. 14/438,327, Response filed Aug. 24, 2016 to Restriction Requirement dated Jul. 12, 2016", 9 pgs.
"U.S. Appl. No. 14/438,327, Response filed Dec. 15, 2017 to Non Final Office Action dated Sep. 29, 2017", 16 pgs.
"U.S. Appl. No. 14/438,327, Response filed Dec. 28, 2016 to Non Final Office Action dated Oct. 6, 2016", 13 pgs.
"U.S. Appl. No. 14/438,327, Restriction Requirement dated Jul. 12, 2016", 9 pgs.
"U.S. Appl. No. 16/135,436, Response filed Nov. 14, 2018 to Restriction Requirement dated Nov. 2, 2018", 10 pgs.
"U.S. Appl. No. 16/135,436, Restriction Requirement dated Nov. 2, 2018", 7 pgs.
"U.S. Appl. No. 16/135,472, Response filed Nov. 14, 2018 to Restriction Requirement dated Nov. 2, 2018", 10 pgs.
"U.S. Appl. No. 16/135,472, Restriction Requirement dated Nov. 2, 2018", 5 pgs.
"Chinese Application Serial No. 201380055869.X, Office Action dated May 26, 2016", w/English Translation, 6 pgs.
"Chinese Application Serial No. 201380055869.X, Office Action dated Jun. 19, 2017", With English Translation, 13 pgs.
"Chinese Application Serial No. 201380055869.X, Office Action dated Nov. 27, 2017", W/English Translation, 13 pgs.
"Chinese Application Serial No. 201380055869.X, Office Action dated Dec. 15, 2016", with English Translation, 20 pgs.
"Chinese Application Serial No. 201380055869.X, Respone filed Apr. 12, 2018 to Office Action dated Nov. 27, 2017", w/ English Claims, 17 pgs.
"Chinese Application Serial No. 201380055869.X, Response filed Sep. 4, 2017 to Office Action dated Jun. 19, 2017", w/ English Claims, 17 pgs.
"Chinese Application Serial No. 201380055869.X, Response filed Sep. 9, 2016 to Office Action dated May 26, 2016", (With English Translation), 18 pgs.
"Chinese Application Serial No. 201380055869.X, Response filed Feb. 28, 2017 to Office Action dated Dec. 15, 2016", w/ English Claims, 21 pgs.
"European Application Serial No. 13848400.1, Communication Pursuant to Article 94(3) EPC dated Apr. 9, 2018", 7 pgs.
"European Application Serial No. 13848400.1, Extended European Search Report dated Apr. 28, 2016", 8 pgs.
"European Application Serial No. 13848400.1, Response filed Sep. 14, 2018 to Communication Pursuant to Article 94(3) EPC dated Apr. 9, 2018", 42 pgs.
"European Application Serial No. 13848400.1, Response filed Oct. 14, 2016 to Extended European Search Report dated Apr. 28, 2016", 17 pgs.
"European Application Serial No. 13848400.1, Response filed Oct. 19, 2015 to Communication pursuant to Rules 161(1) and 162 EPC dated Jun. 2, 2015", 17 pgs.
"European Application Serial No. 16783856.4, Response filed Jun. 22, 2018 to Communication pursuant to Rules 161(2) & 162 EPC dated Dec. 13, 2017", 11 pgs.
"International Application Serial No. PCT/US2013/064842, International Preliminary Report on Patentability dated May 7, 2015", 12 pgs.
"International Application Serial No. PCT/US2013/064842, International Search Report dated Jan. 17, 2014", 3 pgs.
"International Application Serial No. PCT/US2013/064842, Written Opinion dated Jan. 17, 2014", 10 pgs.
"International Application Serial No. PCT/US2016/028652, International Preliminary Report on Patentability dated Nov. 2, 2017", 10 pgs.
"International Application Serial No. PCT/US2016/028652, International Search Report dated Jul. 26, 2016", 2 pgs.
"International Application Serial No. PCT/US2016/028652, Written Opinion dated Jul. 26, 2016", 8 pgs.
"International Application Serial No. PCT/US2018/031083, International Search Report dated Jul. 27, 2018", 4 pgs.
"International Application Serial No. PCT/US2018/031083, Written Opinion dated Jul. 27, 2018", 33 pgs.
"Japanese Application Serial No. 2015-539651, Examiners Decision of Final Refusal dated Nov. 21, 2017", w/ English Translation, 13 pgs.
"Japanese Application Serial No. 2015-539651, Office Action dated May 15, 2018", w/English Translation, 15 pgs.
"Japanese Application Serial No. 2015-539651, Office Action dated Jul. 11, 2017", w/English Translation, 10 pgs.
"Japanese Application Serial No. 2015-539651, Response filed Mar. 20, 2018 to Examiners Decision of Final Refusal dated Nov. 21, 2017", w/ English Claims, 34 pgs.
"Japanese Application Serial No. 2015-539651, Response filed Sep. 6, 2017 to Office Action dated Jul. 11, 2017", w/ English claims, 15 pgs.
"Japanese Application Serial No. 2017-555548, Office Action dated Aug. 21, 2018", w/ English translation, 8 pgs.
"Japanese Application Serial No. 2017-555548, Response filed Nov. 20, 2018 to Office Action dated Aug. 21, 2018", w/English Claims, 11 pgs.
Daughtry, et al., "Balloon Dilation of the Ureter: A Means to Facilitate Passage of Ureteral and Renal Calculi", The Journal of Urology, vol. 136, (1986), 1063-1065.
Daughtry, et al., "Balloon dilation of urethral strictures", Urology, vol. 31, (1988), 231-233.
Lukacs, B, et al., "One-year follow-up of 2829 patients with moderate to severe lower urinary tract symptoms treated with alt uzosin in general practice according to IPSS and a health-related quality-of-life questionnaire", BPM Group in General Practice, Urology; 55(4), (2000), 7 pgs.
Shin, et al., "Tissue Hyperplasia: Influence of a Paclitaxel-eluting Covered Stent-Preliminary Study in a Canine Urethral Model", Radiology, (2005), 438-444.
"U.S. Appl. No. 14/438,327, Response filed Apr. 16, 2019 to Non Final Office Action dated Jan. 28, 2019", 29 pgs.
"U.S. Appl. No. 16/135,436, Notice of Non-Responsive Amendment dated Mar. 8, 2019", 2 pgs.
"U.S. Appl. No. 16/135,436, Response filed Mar. 28, 2019 to Notice of Non-Responsive Amendment dated Mar. 8, 2019", 10 pgs.
"U.S. Appl. No. 16/135,472, Notice of Non Responsive Amendment dated Mar. 8, 2019", 2 pgs.
"U.S. Appl. No. 16/135,472, Response filed Mar. 28, 2019 to Notice of Non Responsive Amendment dated Mar. 8, 2019", 10 pgs.
"Japanese Application Serial No. 2018-052874, Office Action dated Jan. 29, 2019", w/ English translation, 15 pgs.
Yazdani, Saami K, et al., "Vascular, Downstream, and Pharmacokinetic Responses to Treatment with a Low Dose Drug-Coated Balloon in a Swine Femoral Artery Model", Catheterization and Cardiovascular Interventions 83:132-140, (2014), 132-140.
"U.S. Appl. No. 16/135,436, Response filed Aug. 21, 2019 to Non Final Office Action dated Jul. 29, 2019", 18 pgs.

(56) References Cited

OTHER PUBLICATIONS

"U.S. Appl. No. 16/135,472, Response filed Aug. 21, 2019 to Non Final Office Action dated Jul. 30, 2019", 23 pgs.
"Japanese Application Serial No. 2018-052874, Response filed May 14, 2019 to Office Action dated Jan. 29, 2019", w English claims, 24 pgs.
Shiel Jr, William C, "Definition of stricture", [Online] Retrieved from the internet:https: www.medicinenet.com scriptmain art.asp?articlekey= 166621, (2019), 1 pg.
"U.S. Appl. No. 16/135,436, Non Final Office Action dated Jul. 29, 2019", 38 pgs.
"U.S. Appl. No. 16/135,472, Non Final Office Action dated Jul. 30, 2019", 40 pgs.
"U.S. Appl. No. 14/438,327, Final Office Action dated Aug. 9, 2019", 20 pgs.
"European Application Serial No. 13848400.1, Communication Pursuant to Article 94(3) EPC dated Jun. 4, 2019", 9 pgs.
"U.S. Appl. No. 14/438,327, Examiner Interview Summary dated Feb. 12, 2020", 3 pgs.
"U.S. Appl. No. 14/438,327, Non Final Office Action dated Jan. 7, 2020", 11 pgs.
"U.S. Appl. No. 14/438,327, Response filed Feb. 7, 2020 to Non Final Office Action dated Jan. 7, 2020", 13 pgs.
"U.S. Appl. No. 14/438,327, Response filed Dec. 3, 2019 to Final Office Action dated Aug. 9, 2019", 32 pgs.
"U.S. Appl. No. 16/135,436, Final Office Action dated Nov. 29, 2019", 41 pgs.
"U.S. Appl. No. 16/135,436, Response filed Jan. 13, 2020 to Final Office Action dated Nov. 29, 2019", 22 pgs.
"U.S. Appl. No. 16/135,472, Final Office Action dated Nov. 29, 2019", 43 pgs.
"U.S. Appl. No. 16/135,472, Response filed Jan. 13, 2020 to Final Office Action dated Nov. 29, 2019", 27 pgs.
"Chinese Application Serial No. 201380055869.X, Notice of Reexamination dated Nov. 21, 2019", w/ English Translation, 8 pgs.
"European Application Serial No. 13848400.1, Response filed Dec. 16, 2019 to Communication Pursuant to Article 94(3) EPC dated Jun. 4, 2019", 30 pgs.
"Japanese Application Serial No. 2018-052874, Office Action dated Oct. 1, 2019", w/ English translation, 6 pgs.
Donatucci, Craig F, et al., "Randomized Clinical Trial Comparing Balloon Dilatation to Transurethral Resection of Prostate for Benign Prostatic Hyperplasia", Adult Urology vol. 4 2, No. 1, (Jul. 1993), 42-49.
Goldenberg, S L, "Balloon Dilatation of the Prostate", Alternate Methods in the Treatment of Benign Prostatic Hyperplasia, (1993), 97-119.

Huang, Weigua, et al., "Effect of transurethral split of the prostate using a double-columnar balloon catheter for benign prostatic hyperplasia", Medicine 95:40, (Mar. 1, 2016), 4 pgs.
"U.S. Appl. No. 15/568,614, Restriction Requirement dated Feb. 8, 2019", 9 pgs.
"U.S. Appl. No. 15/568,614, Response filed Mar. 20, 2019 to Restriction Requirement dated Feb. 8, 2019", 8 pgs.
"Japanese Application Serial No. 2017-555548, Examiners Decision of Final Refusal dated Mar. 26, 2019", w English translation, 5 pgs.
"European Application Serial No. 16783856.4, Extended European Search Report dated Nov. 9, 2018", 7 pgs.
"European Application Serial No. 16783856.4, Response filed May 28, 2019 to Extended European Search Report dated Nov. 9, 2018", 16 pgs.
"U.S. Appl. No. 15/568,614, Notice of Non-Responsive Amendment dated Jul. 1, 2019", 2 pgs.
"U.S. Appl. No. 15/568,614, Response filed Jul. 9, 2019 to Non-Responsive Amendment dated Jul. 1, 2019 and Restriction Requirement dated Feb. 8, 2019", 8 pgs.
"Japanese Application Serial No. 2017-555548, Respone filed Jul. 26, 2019 to Examiners Decision of Final Refusal dated Mar. 26, 2019", w English Claims, 19 pgs.
"U.S. Appl. No. 16/519,720, Restriction Requirement dated Oct. 18, 2019", 5 pgs.
"U.S. Appl. No. 16/519,720, Response filed Oct. 31, 2019 to Restriction Requirement dated Oct. 18, 2019", 10 pgs.
"U.S. Appl. No. 15/568,614, Non Final Office Action dated Nov. 18, 2019", 22 pgs.
"U.S. Appl. No. 16/519,677, Restriction Requirement dated Nov. 20, 2019", 5 pgs.
"U.S. Appl. No. 16/519,677, Response filed Dec. 13, 2019 to Restriction Requirement dated Nov. 20, 2019", 10 pgs.
"Drug Coated Balloon Catheters for Nonvascular Strictures".
"U.S. Appl. No. 16/519,720, Non Final Office Action dated Feb. 6, 2020", 23 pgs.
"U.S. Appl. No. 15/568,614, Response filed Feb. 10, 2020 to Non Final Office Action dated Nov. 18, 2019", 17 pgs.
"U.S. Appl. No. 16/135,436, Non Final Office Action dated Mar. 5, 2020", 48 pgs.
"U.S. Appl. No. 16/135,472, Non Final Office Action dated Mar. 19, 2020", 56 pgs.
"U.S. Appl. No. 16/519,677, Non Final Office Action dated Mar. 19, 2020", 31 pgs.
"U.S. Appl. No. 16/135,436, Response filed Apr. 6, 2020 to Non Final Office Action dated Mar. 5, 2020", 21 pgs.
"U.S. Appl. No. 16/135,436, Examiner Interview Summary dated Apr. 8, 2020", 3 pgs.

* cited by examiner

DRUG COATED BALLOON CATHETERS FOR NONVASCULAR STRICTURES

PRIORITY

This application is a continuation of U.S. application Ser. No. 14/438,327, filed Apr. 24, 2015, which is a U.S. National Stage Filing under 35 U.S.C 371 from International Application No. PCT/US2013/064842, filed Oct. 14, 2013, which claims the benefit of priority from U.S. Provisional Application No. 61/795,790, filed Oct. 26, 2012, all of which are incorporated by reference herein in their entirety.

FIELD OF THE INVENTION

Embodiments of the present invention relate to drug coated medical devices, such as drug coated balloon catheters, and methods for treatment of nonvascular strictures of body lumens. The nonvascular strictures include benign prostatic hyperplasia (BPH), urethral strictures, ureteral strictures, prostate cancer, esophageal strictures, sinus strictures, biliary tract strictures, asthma and chronic obstructive pulmonary disease (COPD). The methods involve delivering of anti-inflammatory and anti-proliferate drugs (rapamycin or paclitaxel and their analogues) to the diseases.

BACKGROUND OF THE INVENTION

Benign prostatic hyperplasia is a non-cancerous enlargement of the prostate gland, affecting more than 50% percent of men over the age of 60. The prostate early in life is the size and shape of a walnut and weight about 20 grams. Prostate enlargement appears to be a normal process. With age, the prostate gradually increases in size to twice or more its normal size. As the prostate grows, it presses against and narrows the urethra, causing a urinary obstruction that makes it difficult to urinate.

Male urethral stricture disease occurred at a rate as high as 0.6% in some populations. Urethral stricture diseases appeared to be more common in the elderly population. The patients with the strictures experience moderate complications, such as bother from lower urinary tract voiding symptoms, recurrent urinary tract infection and the need for repeat urethral procedures such as dilation or urethrotomy.

Ureteral strictures of upper urinary tract are either congenital or acquired. Congenital ureteral strictures are most commonly located at the ureteropelvic junction. Most of ureteral strictures are acquired and usually are iatrogenic. The most common etiology of the ureteral strictures is injury during endoscopic, open, or laparoscopic surgical procedures.

Esophageal strictures are a problem commonly encountered in gastroenterological medicine and can be caused by malignant or benign lesions. Dysphagia is the symptom experienced by all patients. Most of these patients require palliative treatment to relieve the dysphagia.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S. Chronic bronchitis is inflammation of the bronchial airways. The bronchial airways connect the trachea with the lungs. When inflamed, the bronchial tubes secrete mucus, causing a chronic cough. Emphysema is an overinflation of the alveoli, or air sacs in the lungs. This condition causes shortness of breath.

Asthma is a chronic respiratory disease characterized by inflammation of the airways, excess mucus production and airway hyper responsiveness, and a condition in which airways narrow excessively or too easily respond to a stimulus. Asthma episodes or attacks cause narrowing of the airways, which make breathing difficult. Asthma attacks can have a significant impact on a patient's life, limiting participation in many activities. In severe cases, asthma attacks can be life threatening. Presently, there is no known cure for asthma.

Chronic sinusitis is an inflammation of the membrane lining of one or more paranasal sinuses. Chronic sinusitis lasts longer than three weeks and often continues for months. In cases of chronic sinusitis, there is usually tissue damage. According to the Center for Disease Control (CDC), thirty seven million cases of chronic sinusitis are reported annually.

One of the most common treatments of the strictures described above is balloon catheter dilation. The balloon dilation usually results in symptomatic relief, however, the effect may not persist and recurrent strictures do occur. Repeated the balloon dilations or surgical procedures are often used to treat the recurrent strictures.

The causes of coronary heart disease and the strictures are neointimal proliferation of smooth muscle in arterial vessels and in walls of body lumen. One aspect of the invention is to deliver paclitaxel or rapamycin and their analogues to the wall of body lumen to treat the narrowing and strictures. Drug coated stents and drug coated balloon catheters with these drugs have been approved for inhibiting the growth of the smooth muscle cells in vascular arterial vessels.

The present invention provides new methods for treatments of nonvascular diseases of benign prostatic hyperplasia (BPH) strictures, urethral strictures, ureteral strictures, prostate cancer, esophageal strictures, biliary tract strictures, asthma and chronic obstructive pulmonary disease (COPD) to have a long term persist effect. The new methods will prevent renarrowing and recurrent strictures in years. The methods involve delivering of anti-inflammatory and anti-proliferate drugs (rapamycin or paclitaxel and their analogues) and an additive to a target tissue. Embodiments of the present invention provide a medical device coating formulation comprising a drug for treatment of the nonvascular strictures, and an additive that enhances absorption of the drug into tissue of body lumens.

SUMMARY OF THE INVENTION

Embodiments of the present invention are directed to the treatment of nonvascular strictures of the body lumens by delivering of an effective amount of anti-inflammatory and anti-proliferate drugs (rapamycin or paclitaxel and their analogues) to a target tissue. The nonvascular strictures include benign prostatic hyperplasia (BPH), urethral strictures, ureteral strictures, prostate cancer, esophageal strictures, sinus strictures, biliary tract strictures, asthma and chronic obstructive pulmonary disease (COPD). The treatment is intended for a variety of animals, such as premature neonates to adult humans.

The present inventor has found that coating the exterior surface of a medical device, and particularly of a balloon catheter or a stent, for example, with a layer comprising a therapeutic agent and an additive that has both a hydrophilic part and a drug affinity part is useful in solving the problems associated with the coatings discussed above. The drug affinity part is a hydrophobic part and/or has an affinity to the therapeutic agent by hydrogen bonding and/or van der Waals interactions. Surprisingly, the present inventor has found that the at least one additive according to embodiments of the present invention, which comprises a hydrophilic part and a drug affinity part, in combination with a therapeutic agent, forms an effective drug delivery coating on a medical device without the use of oils and lipids, thereby avoiding the lipolysis dependence and other disadvantages of conventional oil-based coating formulations. Moreover, the additives according to embodiments of the present invention facilitate rapid drug elution and superior permeation of drug into tissues at a disease site. Thus, coatings according to embodiments of the present invention provide an enhanced rate and/or extent of absorption of the hydrophobic therapeutic agent in diseased tissues of the vasculature or other body lumen. In embodiments of the present invention, the coated device delivers therapeutic agent to nonvascular tissues during a very brief deployment time of less than 10 minutes, less than 2 minutes, and reduces renarrowing and reoccurring of the strictures of a nonvascular body lumen.

In one embodiment, the present invention relates to a medical device for delivering a therapeutic agent to a nonvascular tissue, the device comprising a layer overlying an exterior surface of the medical device. The device includes one of a balloon catheter, a perfusion balloon catheter, an infusion catheter such as distal perforated drug infusion tube, a perforated balloon, spaced double balloon, porous balloon, and weeping balloon, a cutting balloon catheter, a scoring balloon catheter. Further, the nonvascular tissue includes tissue of one of esophagus, airways, sinus, trachea, colon, biliary tract, urinary tract, prostate, urethral, ureteral, and other nonvascular lumens.

In one embodiment of the medical devices, the additive enhances absorption of the drug into nonvascular tissue of the body lumens. The nonvascular body lumens include esophagus, airways, sinus, trachea, colon, biliary tract, urinary tract, prostate, urethral, ureteral, and other nonvascular lumens. In another embodiment of the medical devices, the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In another embodiment, the drug is not enclosed in micelles or encapsulated in polymer particles.

In one embodiment of the medical devices, the additive is at least one of a surfactant and a chemical compound. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof. In another embodiment, the chemical compound has one or more hydroxyl, amino, carbonyl, carboxyl, acid, amide or ester groups. In another embodiment, the chemical compound having one or more hydroxyl, amino, carbonyl, carboxyl, acid, amide or ester groups is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In another embodiment, the additive is chosen from p-isononylphenoxypolyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.

In one embodiment, the surfactant is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterols and derivatives thereof, polyethylene glycol sorbitan fatty acid esters, polyethylene glycol alkyl ethers, polyethylene glycol alkyl phenols, polyoxyethylene-polyoxypropylene block copolymers, and sorbitan fatty acid esters. In another embodiment, the surfactant is chosen from esters of lauric acid, oleic acid, and stearic acid, PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate, PEG-32 dioleate, PEG-25 trioleate, PEG-60 corn glycerides, PEG-60 almond oil, PEG-40 palm kernel oil, PEG-8 caprylic/capric glycerides, and PEG-6 caprylic/capric glycerides, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, PEG-20 almond glycerides, polyglyceryl oleate, polyglyceryl-2 dioleate, polyglyceryl-10 trioleate, polyglyceryl stearate, polyglyceryl laurate, polyglyceryl myristate, polyglyceryl palmitate, and polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, polyglyceryl polyricinoleate, propylene glycol monolaurate, propylene glycol ricinoleate, propylene glycol monooleate, propylene glycol dicaprylate/dicaprate, propylene glycol dioctanoate, PEG-20 sorbitan monolaurate, PEG-20 sorbitan monopalmitate, PEG-20 sorbitan monostearate, PEG-20 sorbitan monooleate, PEG-10-100 nonyl phenol, PEG-15-100 octyl phenol ether, Tyloxapol, octoxynol, nonoxynol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucop-yranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside, sorbitan monolaurate, sorbitan monopalmitate, sorbitan monooleate, sorbitan monostearate, benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, sodium taurocholate, and derivatives thereof.

In one embodiment, the chemical compound having one or more hydroxyl, amino, carbonyl, carboxyl, acid, amide or ester groups is chosen from cystine, tyrosine, tryptophan, leucine, isoleucine, phenylalanine, asparagine, aspartic acid, glutamic acid, and methionine (Aminoacids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, L-ascorbic acid and its salt, D-glucoascorbic acid and its salt, tromethamine, triethanolamine, diethanolamine, meglumine, glucamine, amine alcohols, glucoheptonic acid, glucomic acid, gluconolactone, D-glucoheptono-1,4-lactone, glucooctanoic lactone, gulonic acid lactone, mannoic lactone, erythronic acid lactone, ribonic acid lactone, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, acetaminophen, ibuprofen, retinoic acid, lysine acetate, gentisic acid, catechin, catechin gallate, tiletamine, ketamine, propofol, lactic acids, acetic acid, salts of any organic acid and organic amine, lysine/glutamic acid, lysine acetate, lactobionic acid/meglumine, lactobionic acid/tromethanemine, lactobionic acid/diethanolamine, lactic acid/meglumine, lactic acid/tromethanemine, lactic acid/diethanolamine, gentisic acid/meglumine, gentisic acid/tromethanemine, gensitic acid/diethanolamine, vanillic acid/meglumine, vanillic acid/tromethanemine, vanillic acid/diethanolamine, benzoic acid/meglumine, benzoic acid/tromethanemine, benzoic acid/diethanolamine, acetic acid/meglumine, acetic acid/tromethanemine, acetic acid/diethanolamine, polyglycidol, glycerols, multiglycerols, and derivatives thereof.

In one embodiment, the additive is chosen from PEG fatty esters and alcohols, glycerol fatty esters, sorbitan fatty esters, PEG glyceryl fatty esters, PEG sorbitan fatty esters, sugar fatty esters, PEG sugar esters, vitamins and derivatives, aminoacids, multiaminoacids and derivatives, peptides, polypeptides, proteins, quaternary ammonium salts, organic acids, salts and anhydrides. In another embodiment, the additive in the coating layer overlying the surface of the balloon is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, L-ascorbic acid and its salt, D-glucoascorbic acid and its salt, triethanolamine, diethanolamine, meglumine, tromethamine, glucamine, glucosamine, glucoheptonic acid, glucomic acid, gluconolactone, D-glucoheptono-1,4-lactone, glucooctanoic lactone, gulonic acid lactone, mannoic lactone, erythronic acid lactone, ribonic acid lactone, glucosamine, glutamic acid, benzyl alcohol, benzoic acid, hydroxybenzoic acid, vanillin, vanillic acid, vanillic acid diethylamide, lysine acetate salt, gentisic acid, lactobionic acid, lactitol, acetaminophen, ibuprofen, catechin, catechin gallate, methyl paraben, ethyl paraben, propyl paraben, butyl paraben, tiletamine, ketamine, propofol, lactic acids, acetic acid, salts of any organic acid and amine above described, polyglycidol, glycerols and multiglycerols (chemical compounds with multiple hydroxyl, amino, carbonyl, carboxyl, or ester moieties).

In another aspect of this embodiment, the ionic surfactant is chosen from benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, and dialkylesters of sodium sulfonsuccinic acid, sodium dioctyl sulfosuccinate, sodium cholate, and sodium taurocholate.

In another embodiment, the medical device further comprises a dimethylsulfoxide solvent layer, wherein the dimethylsulfoxide solvent layer is overlying the surface of the layer.

In one embodiment of the medical device, the device is capable of releasing the therapeutic agent and the additive and delivering therapeutic agent to the tissue in about 0.1 to 10 minutes. In one embodiment, the concentration of the therapeutic agent in the layer is from 1 to 20 µg/mm$^2$. In one embodiment, the concentration of the therapeutic agent in the layer is from 2 to 10 µg/mm$^2$. In one embodiment, the therapeutic agent is not water-soluble.

In one embodiment, the additive enhances release of the therapeutic agent off the balloon. In another embodiment, the additive enhances penetration and absorption of the therapeutic agent in tissue. In another embodiment, the additive has a water and ethanol solubility of at least 1 mg/ml and the therapeutic agent is not water-soluble.

In another embodiment of the medical device, the layer overlying the exterior surface of the medical device comprises a therapeutic agent and at least two additives, wherein each of the additives comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water. In another aspect of this embodiment, the device further comprises a top layer overlying the surface of the layer overlying the exterior surface of the medical device to reduce loss of drug during transit through a body to the target tissue.

In another embodiment of the medical device, the layer overlying the exterior surface of the medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive reduces crystal size and number of particles of the therapeutic agent, and wherein the additive is water-soluble and the therapeutic agent is not water-soluble.

In another embodiment of the medical device, the layer overlying the exterior surface of the medical device comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive has a fatty chain of an acid, ester, ether, or alcohol, wherein the fatty chain can directly insert into lipid membrane structures of the tissue, and wherein the therapeutic agent is not water-soluble.

In another embodiment of the medical device, the layer overlying the exterior surface of the medical device comprises a therapeutic agent and an additive, wherein the additive comprises a hydrophilic part and a hydrophobic part, wherein the additive can penetrate into and rearrange lipid membrane structures of the tissue, and wherein the therapeutic agent is not water-soluble and is not enclosed in micelles or encapsulated in polymer particles.

In another embodiment of the medical device, the layer overlying the exterior surface of the medical device comprises a therapeutic agent and an additive, wherein the additive comprises a hydrophilic part and a drug affinity part, wherein the additive has a fatty chain of an acid, ester, ether, or alcohol, wherein the fatty chain directly inserts into lipid membrane structures of tissue, wherein the additive has one or more functional groups which have affinity to the drug by hydrogen bonding and/or van der Waals interactions (the functional groups include hydroxyl, ester, amide, carboxylic acid, primary, second, and tertiary amine, carbonyl, anhydrides, oxides, and amino alcohols), wherein the therapeutic agent is not water-soluble and is not enclosed in micelles or encapsulated in polymer particles, and wherein the layer does not include a polymer, and the layer does not include an iodine covalent bonded contrast agent.

In yet another embodiment, the present invention relates to a medical device coating for delivering a drug to a tissue that is prepared from a mixture. In one aspect of this embodiment, the coating is prepared from a mixture comprising an organic phase containing drug particles dispersed therein and an aqueous phase containing a water-soluble additive. In one aspect of this embodiment, the water-soluble additive is chosen from polyethylene glycol, polyvinyl alcohol, polyvinylpyrrolidinone, polypeptides, water-soluble surfactants, water-soluble vitamins, and proteins. In another aspect of this embodiment, the preparation of the mixture includes homogenization under high shear conditions and optionally under pressure.

In another embodiment, the present invention relates to a balloon catheter for delivering a therapeutic agent to a body lumen, the catheter comprising a coating layer overlying an exterior surface of a balloon. In one embodiment of the balloon catheter, the coating layer comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is water-soluble, and wherein the additive is at least one of a surfactant and a chemical compound, and wherein the chemical compound has a molecular weight of from 50 to 750.

In another embodiment of the balloon catheter, the coating layer comprises a therapeutic agent and an additive, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the additive is at least one of a surfactant and a chemical compound, and wherein the chemical compound has more than four hydroxyl groups. In one aspect of this embodiment, the chemical compound having more than four hydroxyl groups has a melting point of 120° C. or less, and the chemical compound is an alcohol or an ester.

In one embodiment of the balloon catheter, the coating layer overlying an exterior surface of the exterior surface of the medical device consists essentially of the therapeutic agent and the additive. In another embodiment, the layer overlying the exterior surface of the medical device does not include an iodine covalent bonded contrast agent.

In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof. In one embodiment, the chemical compound has one or more hydroxyl, amino, carbonyl, carboxyl, acid, amide or ester groups. In one embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment of the balloon catheters, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterols and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof.

In another embodiment of the balloon catheters, the additive is chosen from esters of lauric acid, oleic acid, and stearic acid, PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, and PEG-20 oleate. In another embodiment, the additive is chosen from PEG-20 dilaurate, PEG-20 dioleate, PEG-20 distearate, PEG-32 dilaurate and PEG-32 dioleate. In another embodiment of the method, the additive is chosen from PEG-20 glyceryl laurate, PEG-30 glyceryl laurate, PEG-40 glyceryl laurate, PEG-20 glyceryl oleate, and PEG-30 glyceryl oleate. In another embodiment of the method, the additive is chosen from PEG-25 trioleate, PEG-60 corn glycerides, PEG-60 almond oil, PEG-40 palm kernel oil, PEG-8 caprylic/capric glycerides, and PEG-6 caprylic/capric glycerides, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, and PEG-20 almond glycerides.

In another embodiment of the balloon catheters, the additive is chosen from polyglyceryl oleate, polyglyceryl-2 dioleate, polyglyceryl-10 trioleate, polyglyceryl stearate, polyglyceryl laurate, polyglyceryl myristate, polyglyceryl palmitate, and polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, and polyglyceryl polyricinoleate. In another embodiment of the method, the additive is chosen from propylene glycol monolaurate, propylene glycol ricinoleate, propylene glycol monooleate, propylene glycol dicaprylate/dicaprate, and propylene glycol dioctanoate. In another embodiment of the balloon catheters, the additive is PEG-24 cholesterol ether. In another embodiment of the balloon catheters, the additive is chosen from sterol polyethylene glycol derivatives.

In one embodiment, the present invention relates to a method for treating a nonvascular stricture of body lumen comprising inserting a balloon catheter comprising a coating layer into an body stricture, wherein the stricture is one of benign prostatic hyperplasia (BPH), urethral strictures, ureteral strictures, prostate cancer, esophageal strictures, sinus strictures, biliary tract strictures, asthma and chronic obstructive pulmonary disease (COPD), wherein the coating layer comprises a drug and an additive, inflating the balloon catheter and releasing the drug to a wall of the stricture, deflating the balloon; and withdrawing the balloon catheter, wherein the residual drug is about 1 to 45% of the total loading drug on the balloon catheter. In one aspect of this embodiment, the additive enhances absorption of the drug into tissue of the nonvascular body lumen. In another embodiment of the method, the additive is chosen from PEG-20 sorbitan monolaurate, PEG-20 sorbitan monopalmitate, PEG-20 sorbitan monostearate, and PEG-20 sorbitan monooleate. In another embodiment of the method, the additive is chosen from PEG-3 oleyl ether and PEG-4 lauryl ether. In another embodiment of the method, the additive is chosen from sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucop-yranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, and octyl-β-D-thioglucopyranoside.

In another embodiment of the method, the additive is chosen from PEG-10-100 nonyl phenol, PEG-15-100 octyl phenol ether, Tyloxapol, octoxynol, and nonoxynol. In another embodiment of the method, the additive is chosen from poloxamer 108, poloxamer 188, poloxamer 217, poloxamer 238, poloxamer 288, poloxamer 338, and poloxamer 407. In another embodiment of the method, the additive is chosen from poloxamer 124, poloxamer 182, poloxamer 183, poloxamer 212, poloxamer 331, and poloxamer 335. In another embodiment of the method, the additive is chosen from sorbitan monolaurate, sorbitan monopalmitate, sorbitan monooleate, and sorbitan monostearate. In another embodiment of the method, the additive is chosen from alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II), and folic acid.

In another embodiment of the method, the additive is chosen from acetiamine, benfotiamine, pantothenic acid, cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. In another embodiment of the method, the additive is chosen from alanine, arginine, asparagines, aspartic acid, cysteine, glutamic acid, glutamine, glycine, histidine, proline, isoleucine, leucine, lysine, methionine, phenylalanine, serine, threonine, tryptophan, tyrosine, and valine, and salts of any of the foregoing. In another embodiment of the method, the additive is albumin. In another embodiment of the method, the additive is chosen from n-octyl-β-D-glucopyranoside, octoxynol-9, Polysorbates, Tyloxapol, octoxynol, nonoxynol, isononylphenylpolyglycidol, PEG glyceryl monooleate, sorbitan monolaurate, sorbitan monopalmitate, sorbitan monooleate, sorbitan monostearate, polyglyceryl-10 oleate, polyglyceryl-10 laurate, polyglyceryl-10 palmitate, polyglyceryl-10 stearate, L-ascorbic acid, thiamine, maleic anhydride, niacinamide, and 2-pyrrolidone-5-carboxylic acid.

In another embodiment of the method, the additive is chosen from riboflavin, riboflavin-phosphate sodium, Vitamin D3, folic acid, vitamin 12, diethylenetriaminepentaacetic acid dianhydride, ethylenediaminetetraacetic dianhydride, maleic acid and anhydride, succinic acid and anhydride, diglycolic anhydride, glutaric anhydride, L-ascorbic acid, thiamine, nicotinamide, nicotinic acid, 2-pyrrolidone-5-carboxylic acid, cystine, tyrosine, tryptophan, leucine, isoleucine, phenylalanine, asparagine, aspartic acid, glutamic acid, and methionine.

In another embodiment of the method, the additive is chosen from isononylphenylpolyglycidol, PEG glyceryl monooleate, sorbitan monolaurate, sorbitan monopalmitate, sorbitan monooleate, sorbitan monostearate, polyglyceryl-10 oleate, polyglyceryl-10 laurate, polyglyceryl-10 palmitate, and polyglyceryl-10 stearate. In another embodiment of the method, the additive is chosen from L-ascorbic acid, thiamine, maleic acids, niacinamide, and 2-pyrrolidone-5-carboxylic acid. In another embodiment of the method, the additive is chosen from Vitamin D2 and D3.

In one embodiment, the additive is at least one of a surfactant and a chemical compound. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof. In one embodiment, the chemical compound has one or more hydroxyl, amino, carbonyl, carboxyl, acid, amide or ester groups. In one aspect of this embodiment, the chemical compound having one or more hydroxyl, amino, carbonyl, carboxyl, acid, amide or ester groups is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In another aspect of this embodiment, the chemical compound having one or more hydroxyl, amino, carbonyl, carboxyl, acid, amide or ester groups is chosen from cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, L-ascorbic acid and its salt, D-glucoascorbic acid and its salt, tromethamine, triethanolamine, diethanolamine, meglumine, glucamine, amine alcohols, glucoheptonic acid, glucomic acid, gluconolactone, D-glucoheptono-1,4-lactone, glucooctanoic lactone, gulonic acid lactone, mannoic lactone, erythronic acid lactone, ribonic acid lactone, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, acetaminophen, ibuprofen, retinoic acid, lysine acetate, gentisic acid, catechin, catechin gallate, tiletamine, ketamine, propofol, lactic acids, acetic acid, salts of any organic acid and amine above described, lysine/glutamic acid, lysine acetate, lactobionic acid/meglumine, lactobionic acid/tromethanemine, lactobionic acid/diethanolamine, lactic acid/meglumine, lactic acid/tromethanemine, lactic acid/diethanolamine, gentisic acid/meglumine, gentisic acid/tromethanemine, gensitic acid/diethanolamine, vanillic acid/meglumine, vanillic acid/tromethanemine, vanillic acid/diethanolamine, benzoic acid/meglumine, benzoic acid/tromethanemine, benzoic acid/diethanolamine, acetic acid/meglumine, acetic acid/tromethanemine, acetic acid/diethanolamine, polyglycidol, glycerols, multiglycerols and a mixture of the additives, and their derivatives.

In one embodiment, the additive is chosen from p-isononylphenoxypolyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol), and penta(propylene glycol), poly(propylene glycol) oligomers, a block copolymer of polyethylene glycol and polypropylene glycol, and derivatives and combinations thereof.

In one embodiment, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterol and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof. In yet another aspect of this embodiment, the water insoluble drug is chosen from paclitaxel and analogues thereof and rapamycin and analogues thereof.

In one embodiment, the surfactant is chosen from esters of lauric acid, oleic acid, and stearic acid, PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate, PEG-32 dioleate, PEG-20 glyceryl laurate, PEG-30 glyceryl laurate, PEG-40 glyceryl laurate, PEG-20 glyceryl oleate, PEG-30 glyceryl oleate, PEG-25 trioleate, PEG-60 corn glycerides, PEG-60 almond oil, PEG-40 palm kernel oil, PEG-8 caprylic/capric glycerides, PEG-6 caprylic/capric glycerides, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, PEG-20 almond glycerides, polyglyceryl oleate, polyglyceryl-2 dioleate, polyglyceryl-10 trioleate, polyglyceryl stearate, polyglyceryl laurate, polyglyceryl myristate, polyglyceryl palmitate, and polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, and polyglyceryl polyricinoleate, propylene glycol monolaurate, propylene glycol ricinoleate, propylene glycol monooleate, propylene glycol dicaprylate/dicaprate, propylene glycol dioctanoate, PEG-20 sorbitan monolaurate, PEG-20 sorbitan monopalmitate, PEG-20 sorbitan monostearate, PEG-20 sorbitan monooleate, PEG-3 oleyl ether and PEG-4 lauryl ether, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucop-yranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside, PEG-10-100 nonyl phenol, PEG-15-100 octyl phenol ether, Tyloxapol, octoxynol, nonoxynol, sorbitan monolaurate, sorbitan monopalmitate, sorbitan monooleate, sorbitan monostearate, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), n-octyl-β-D-glucopyranoside, octoxynol-9, Polysorbates, Tyloxapol, octoxynol, nonoxynol, isononylphenylpolyglycidol, PEG glyceryl monooleate, sorbitan monolaurate, sorbitan monopalmitate, sorbitan monooleate, sorbitan monostearate, polyglyceryl-10 oleate, polyglyceryl-10 laurate, polyglyceryl-10 palmitate, polyglyceryl-10 stearate, and their derivatives.

In one embodiment, the water insoluble drug is chosen from paclitaxel and analogues thereof and rapamycin and analogues thereof.

In one embodiment, some drugs that are considered particularly suitable for the airway, sinus and other nasal lumens are corticosteroids such as, budesonide, flunisolide, triamcinolone, beclomethasone, fluticasone, mometasone, mometasone furoate, dexamethasone, hydrocortisone, methylprednisolone, prednisone, cotisone, betamethasone, triamcinolone acetonide, or the like.

In one embodiment, the present invention relates to a method for treating a nonvascular body lumen comprising inserting a balloon catheter comprising a coating layer into an body lumen, wherein the body lumen is one of esophagus, airways, sinus, trachea, colon, biliary tract, urinary tract, prostate, urethral, ureteral, and other nonvascular lumens, wherein the coating layer comprises a drug and an additive, inflating the balloon catheter and releasing the drug to a wall of the body lumen, deflating the balloon; and withdrawing the balloon catheter. In another embodiment, the present invention relates to a method for treating a nonvascular stricture of body lumen comprising inserting a balloon catheter comprising a coating layer into a nonvascular strictures of body lumen, wherein the nonvascular strictures of body lumen is one of benign prostatic hyperplasia (BPH), urethral strictures, ureteral strictures, prostate cancer, esophageal strictures, sinus strictures, biliary strictures, asthma and chronic obstructive pulmonary disease (COPD), wherein the coating layer comprises a drug and an additive, inflating the balloon catheter and releasing the drug to a wall of the body lumen, deflating the balloon; and withdrawing the balloon catheter. In one aspect of this embodiment, the additive enhances absorption of the drug into tissue of the nonvascular body lumens. In another aspect of this embodiment, the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. In another aspect of this embodiment, the drug is not enclosed in micelles or encapsulated in polymer particles. In another aspect of this embodiment, the coating layer does not include oil, a lipid, or a polymer. In another aspect of this embodiment, the coating layer does not include a purely hydrophobic additive. In another aspect of this embodiment, the drug is chosen from paclitaxel and analogues thereof and rapamycin and analogues thereof. In another aspect of this embodiment, the additive is chosen from PEG-fatty acids and PEG-fatty acid mono and diesters, polyethylene glycol glycerol fatty acid esters, alcohol-oil transesterification products, polyglyceryl fatty acids, propylene glycol fatty acid esters, sterol and derivatives thereof, polyethylene glycol sorbitan fatty acid esters, polyethylene glycol alkyl ethers, sugars and derivatives thereof, polyethylene glycol alkyl phenols, polyoxyethylene-polyoxypropylene block copolymers, sorbitan fatty acid esters, fat-soluble vitamins and salts thereof, water-soluble vitamins and amphiphilic derivatives thereof, amino acid and salts thereof, oligopeptides, peptides and proteins, and organic acids and esters and anhydrides thereof. In yet another aspect of this embodiment, the drug can be released to the wall of the airway prior to, during, or after an asthma attack. In yet another aspect of this embodiment, the drug can be released to the wall of the esophagus. In yet another aspect of this embodiment, the drug can be released to the wall of the sinus. In yet another aspect of this embodiment, the drug can be released to the wall of the biliary tract. In yet another aspect of this embodiment, the drug can be released to the wall of the urinary tract, prostate, urethral, and ureteral lumens.

In one embodiment, the additive is at least one of a surfactant and a chemical compound. In one embodiment, the chemical compound is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In one embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof.

In one embodiment, the chemical compound has one or more hydroxyl, amino, carbonyl, carboxyl, acid, amide or ester groups. In one aspect of this embodiment, the chemical compound having one or more hydroxyl, amino, carbonyl, carboxyl, acid, amide or ester groups is chosen from amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment, the additive is chosen from p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, trometamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol), and penta(propylene glycol), poly(propylene glycol) oligomers, a block copolymer of polyethylene glycol and polypropylene glycol, and derivatives and combinations thereof.

It is understood that both the foregoing general description and the following detailed description are exemplary and explanatory only and are not restrictive of the present invention as claimed.

DETAILED DESCRIPTION OF EXEMPLARY EMBODIMENTS

Embodiments of the present invention relate to medical devices, including particularly balloon catheters and stents, having a rapid drug-releasing coating and methods for preparing such coated devices. The therapeutic agent according to embodiments of the present invention does not require a delayed or long term release and instead preferably the therapeutic agent and the additive are released in a very short time period to provide a therapeutic effect upon contact with tissue. An object of embodiments of the present invention is to facilitate rapid and efficient uptake of drug by target tissue during transitory device deployment at a target site.

Figure 1:
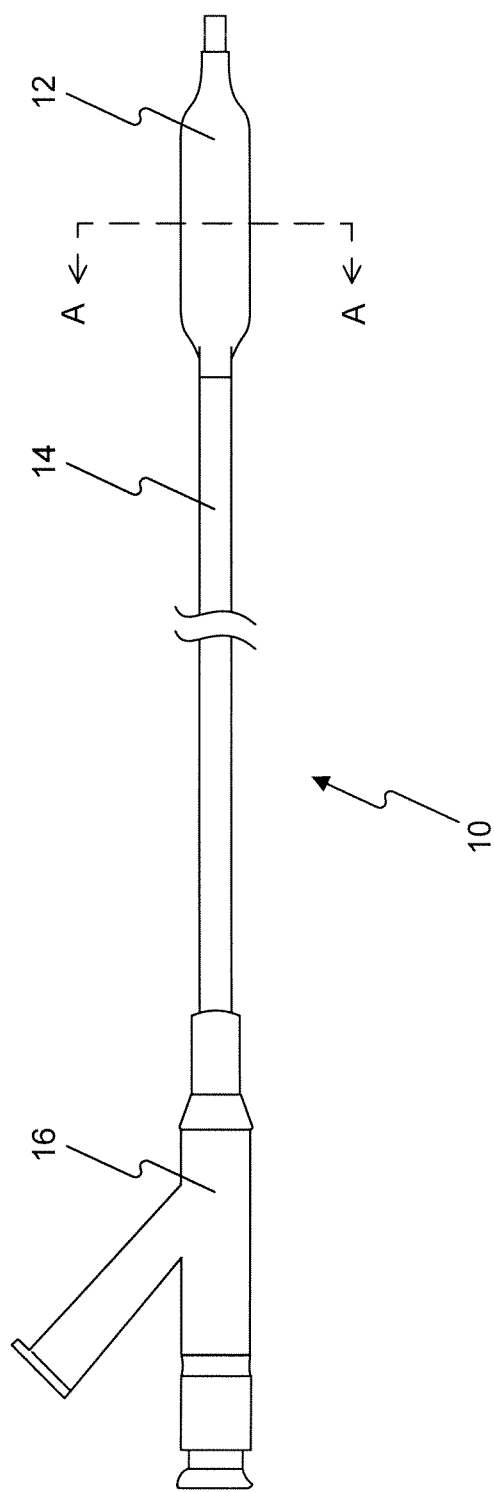
FIG. 1 is a perspective view of an exemplary embodiment of a balloon catheter according to the present invention.

As shown in FIG. 1, in one embodiment, the medical device is a balloon catheter. The balloon catheter may be any suitable catheter for the desired use, including conventional balloon catheters known to one of ordinary skill in the art. For example, balloon catheter 10 may include an expandable, inflatable balloon 12 at a distal end of the catheter 10, a handle assembly 16 at a proximal end of the catheter 10, and an elongate flexible member 14 extending between the proximal and distal ends. Handle assembly 16 may connect to and/or receive one or more suitable medical devices, such as a source of inflation media (e.g., air, saline, or contrast media). Flexible member 14 may be a tube made of suitable biocompatible material and having one or more lumens therein. At least one of the lumens is configured to receive inflation media and pass such media to balloon 12 for its expansion. The balloon catheter may be a rapid exchange or over-the-wire catheter and made of any suitable biocompatible material. The material of balloon 12 is made of one of polyesters, polyamides, nylon 12, nylon 11, polyamide 12, block copolymers of polyether and polyamide, Pebax, polyurethanes, and block copolymers of polyether and polyester.

Figure 2A:
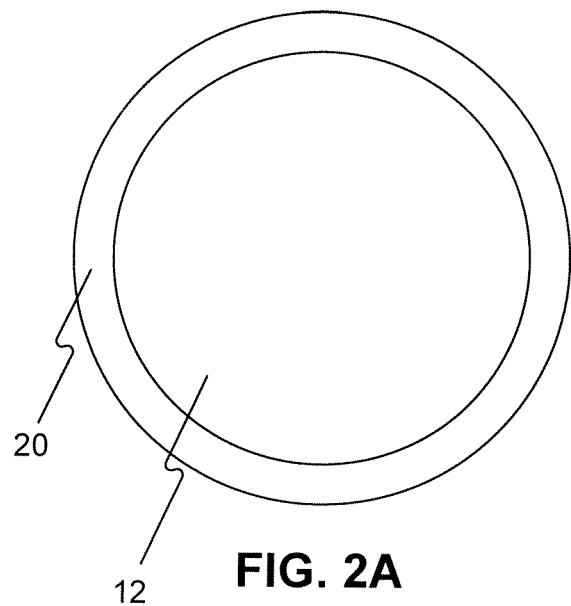
FIGS. 2A-2C are cross-sectional views of different embodiments of the distal portion of the balloon catheter of FIG. 1, taken along line A-A, showing exemplary coating layers.
Figure 2B:
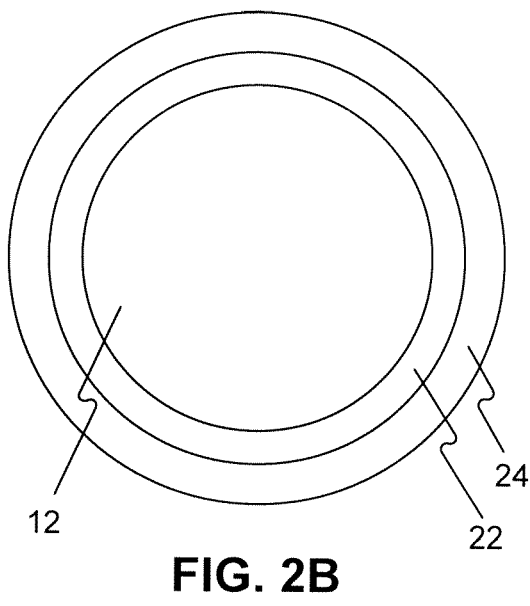
Figure 2C:
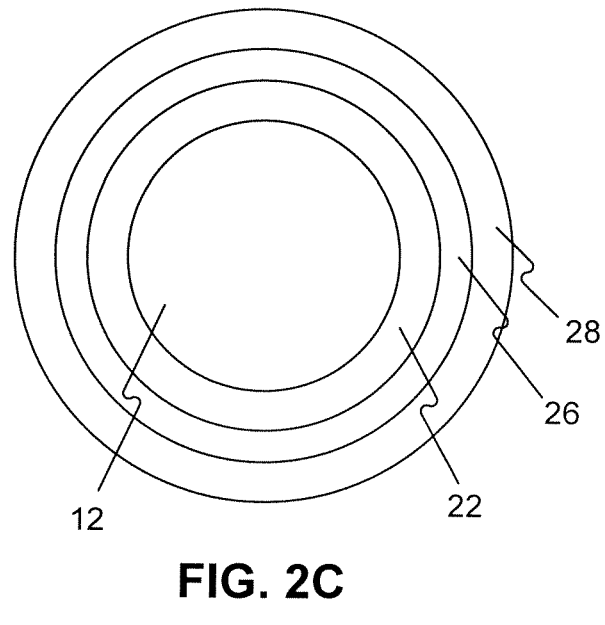

In one embodiment, the present invention provides a medical device for delivering a therapeutic agent to a nonvascular tissue. The device includes a layer applied to an exterior surface of the medical device, such as a balloon catheter or stent, for example. The layer includes a therapeutic agent and an additive. For example, as shown in the embodiment depicted in FIG. 2A, the balloon 12 is coated with a layer 20 that includes a therapeutic agent and an additive. In some embodiments, the layer consists essentially of a therapeutic agent and an additive, i.e., the layer includes only the therapeutic agent and the additive, without any other materially significant components. In some embodiments, the device may optionally include an adherent layer. For example, as shown in the embodiment depicted in FIG. 2B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the medical device, the adherent layer may prevent differential loss of components and maintain drug-to-additive ratio in the coating during transit to a target site for therapeutic intervention. Furthermore, the adherent layer may function to facilitate rapid release of coating layer components off the device surface upon contact with tissues at the target site. In other embodiments, the device may include a top layer. The top layer may reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

Embodiments of the present invention are directed to the treatment of nonvascular strictures of the body lumens by delivering of an effective amount of anti-inflammatory and anti-proliferate drugs (rapamycin or paclitaxel and their analogues). The nonvascular strictures include benign prostatic hyperplasia (BPH), urethral strictures, ureteral strictures, prostate cancer, esophageal strictures, sinus strictures, biliary tract strictures, asthma and chronic obstructive pulmonary disease (COPD). According to embodiments, the method involves delivering of anti-inflammatory and anti-proliferate drugs (rapamycin or paclitaxel and their analogues) via coated medical devices, such as balloon catheters and stents. The anti-inflammatory and anti-proliferate drugs can be coated with the medical device alone or with one or more additives.

In one embodiment, the present invention relates to a method for treating a nonvascular stricture of body lumen comprising inserting a balloon catheter comprising a coating layer into the stricture, wherein the stricture is one of benign prostatic hyperplasia (BPH), urethral strictures, ureteral strictures, prostate cancer, esophageal strictures, sinus strictures, biliary tract strictures, asthma and chronic obstructive pulmonary disease (COPD), wherein the coating layer comprises a drug and an additive, inflating the balloon catheter and releasing the drug to a wall of the stricture, deflating the balloon; and withdrawing the balloon catheter, wherein the residual drug is about 1 to 45% of the total loading drug on the balloon catheter, wherein the drug in the wall of body lumen is about 0.1 to 25% of the total loading drug on the balloon catheter. In one aspect of this embodiment, the additive enhances absorption of the drug into tissue of the nonvascular stricture of body lumen.

In one embodiment, the present invention relates to a method for treating a nonvascular body lumen comprising inserting a balloon catheter comprising a coating layer into an body lumen, wherein the body lumen is one of esophagus, airways, sinus, trachea, colon, biliary tract, urinary tract, prostate, urethral, ureteral, and other nonvascular lumens, wherein the coating layer comprises a drug and an additive, inflating the balloon catheter and releasing the drug to a wall of the body lumen, deflating the balloon; and withdrawing the balloon catheter, wherein the residual drug is about 1 to 45% of the total loading drug on the balloon catheter, wherein the drug in the wall of body lumen is about 0.1 to 25% of the total loading drug on the balloon catheter. In one aspect of this embodiment, the additive enhances absorption of the drug into tissue of the nonvascular body lumens. In another aspect of this embodiment, the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions.

Additive

The additive of embodiments of the present invention has two parts. One part is hydrophilic and the other part is a drug affinity part. The drug affinity part is a hydrophobic part and/or has an affinity to the therapeutic agent by hydrogen bonding and/or van der Waals interactions. The drug affinity part of the additive may bind the lipophilic drug, such as rapamycin or paclitaxel. The hydrophilic portion accelerates diffusion and increases permeation of the drug into tissue. It may facilitate rapid movement of drug off the medical device during deployment at the target site by preventing hydrophobic drug molecules from clumping to each other and to the device, increasing drug solubility in interstitial spaces, and/or accelerating drug lumen through polar head groups to the lipid bilayer of cell membranes of target tissues. The additives of embodiments of the present invention have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present invention, the therapeutic agent is rapidly released after the medical device is brought into contact with tissue and is readily absorbed. For example, certain embodiments of devices of the present invention include drug coated balloon catheters that deliver a lipophilic anti-proliferative pharmaceutical (such as paclitaxel or rapamycin) to nonvascular tissue through brief, direct pressure contact at high drug concentration during balloon angioplasty. The lipophilic drug is preferentially retained in target tissue at the delivery site, where it inhibits hyperplasia and restenosis yet allows endothelialization. In these embodiments, coating formulations of the present invention not only facilitate rapid release of drug from the balloon surface and transfer of drug into target tissues during deployment, but also prevent drug from diffusing away from the device during transit through tortuous arterial anatomy prior to reaching the target site and from exploding off the device during the initial phase of balloon inflation, before the drug coating is pressed into direct contact with the surface of the vessel wall.

The additive according to certain embodiments has a drug affinity part and a hydrophilic part. The drug affinity part is a hydrophobic part and/or has an affinity to the therapeutic agent by hydrogen bonding and/or van der Waals interactions. The drug affinity part may include aliphatic and aromatic organic hydrocarbon compounds, such as benzene, toluene, and alkanes, among others. These parts are not water soluble. They may bind both hydrophobic drug, with which they share structural similarities, and lipids of cell membranes. They have no covalently bonded iodine. The drug affinity part may include functional groups that can form hydrogen bonds with drug and with itself. The hydrophilic part may include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, may be advantageous since they easily displace water molecules that are hydrogen-bound to polar head groups and surface proteins of cell membranes and may function to remove this barrier between hydrophobic drug and cell membrane lipid. These parts can dissolve in water and polar solvents. These additives are not oils, lipids, or polymers. The therapeutic agent is not enclosed in micelles or liposomes or encapsulated in polymer particles. The additive of embodiments of the present invention has components to both bind drug and facilitate its rapid movement off the medical device during deployment and into target tissues.

The additives in embodiments of the present invention are surfactants and chemical compounds with one or more hydroxyl, amino, carbonyl, carboxyl, acid, amide or ester moieties. The surfactants include ionic, nonionic, aliphatic, and aromatic surfactants. The chemical compounds with one or more hydroxyl, amino, carbonyl, carboxyl, acid, amide or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

As is well known in the art, the terms "hydrophilic" and "hydrophobic" are relative terms. To function as an additive in exemplary embodiments of the present invention, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute] octanol/[solute]water). Compounds with higher log Ps are more hydrophobic, while compounds with lower log Ps are more hydrophilic. Lipinski's rule suggests that pharmaceutical compounds having log P<5 are typically more membrane permeable. For purposes of certain embodiments of the present invention, it is preferable that the additive has log P less than log P of the drug to be formulated (as an example, log P of paclitaxel is 7.4). A greater log P difference between the drug and the additive can facilitate phase separation of drug. For example, if log P of the additive is much lower than log P of the drug, the additive may accelerate the release of drug in an aqueous environment from the surface of a device to which drug might otherwise tightly adhere, thereby accelerating drug delivery to tissue during brief deployment at the site of intervention. In certain embodiments of the present invention, log P of the additive is negative. In other embodiments, log P of the additive is less than log P of the drug. While a compound's octanol-water partition coefficient P or log P is useful as a measurement of relative hydrophilicity and hydrophobicity, it is merely a rough guide that may be useful in defining suitable additives for use in embodiments of the present invention.

Suitable additives that can be used in embodiments of the present invention include, without limitation, organic and inorganic pharmaceutical excipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The following detailed list of additives useful in the present invention is provided for exemplary purposes only and is not intended to be comprehensive. Many other additives may be useful for purposes of the present invention.

Surfactants

The surfactant can be any surfactant suitable for use in pharmaceutical compositions. Such surfactants can be anionic, cationic, zwitterionic or non-ionic. Mixtures of surfactants are also within the scope of the invention, as are combinations of surfactant and other additives. Surfactants often have one or more long aliphatic chains such as fatty acids that may insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present invention, a higher HLB value is preferred, since increased hydrophilicity may facilitate release of hydrophobic drug from the surface of the device. In one embodiment, the HLB of the surfactant additive is higher than 10. In another embodiment, the additive HLB is higher than 14. Alternatively, surfactants having lower HLB may be preferred when used to prevent drug loss prior to device deployment at the target site, for example in a top coat over a drug layer that has a very hydrophilic additive.

It should be understood that the HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants may be identified that have suitable hydrophilicity or hydrophobicity for use in embodiments of the present invention, as described herein.

PEG-Fatty Acids and PEG-Fatty Acid Mono and Diesters

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Most preferred hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and diesters.

Polyethylene Glycol Glycerol Fatty Acid Esters

Preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil®b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids

Polyglycerol esters of fatty acids are also suitable surfactants for use in embodiments of the present invention. Among the polyglyceryl fatty acid esters, preferred hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Preferred hydrophilic surfactants include polyglyceryl-10 laurate (Nikkol Decaglyn 1-L), polyglyceryl-10 oleate (Nikkol Decaglyn 1-0), and polyglyceryl-10 mono, dioleate (Caprol® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also preferred surfactants.

Propylene Glycol Fatty Acid Esters

Esters of propylene glycol and fatty acids are suitable surfactants for use in embodiments of the present invention. In this surfactant class, preferred hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Sterol and Sterol Derivatives

Sterols and derivatives of sterols are suitable surfactants for use in embodiments of the present invention. Preferred derivatives include the polyethylene glycol derivatives. A preferred surfactant in this class is PEG-24 cholesterol ether (Solulan C-24).

Polyethylene Glycol Sorbitan Fatty Acid Esters

A variety of PEG-sorbitan fatty acid esters are available and are suitable for use as surfactants in embodiments of the present invention. Among the PEG-sorbitan fatty acid esters, preferred surfactants include PEG-20 sorbitan monolaurate (Tween-20), PEG-20 sorbitan monopalmitate (Tween-40), PEG-20 sorbitan monostearate (Tween-60). PEG-20 sorbitan monooleate (Tween-80). Laurate esters are preferred because they have a short lipid chain compared with oleate esters, increasing drug absorption.

Polyethylene Glycol Alkyl Ethers

Ethers of polyethylene glycol and alkyl alcohols are suitable surfactants for use in embodiments of the present invention. Preferred ethers include PEG-3 oleyl ether (Volpo 3) and PEG-4 lauryl ether (Brij 30).

Sugar and its Derivatives

Sugar derivatives are suitable surfactants for use in embodiments of the present invention. Preferred surfactants in this class include sucrose monopalmitate, sucrose monolaurate, decanoyl-N-methylglucamide, n-decyl-.beta.-D-glucopyranoside, n-decyl-.beta.-D-maltopyranoside, n-dodecyl-.beta.-D-glucopyranoside, n-dodecyl-.beta.-D-maltoside, heptanoyl-N-methylglucamide, n-heptyl-.beta.-D-glucopyranoside, n-heptyl-.beta.-D-thioglucoside, n-hexyl-.beta.-D-glucopyranoside, nonanoyl-N-methylglucamide, n-noyl-.beta.-D-glucopyranoside, octanoyl-N-methylglucamide, n-octyl-.beta.-D-glucopyranoside, and octyl-.beta.-D-thioglucopyranoside.

Polyethylene Glycol Alkyl Phenols

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present invention.

Polyoxyethylene-Polyoxypropylene (POE-POP) Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_b(C_2H_4O)_aH$ where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Sorbitan Fatty Acid Esters

Sorbitan esters of fatty acids are suitable surfactants for use in embodiments of the present invention. Among these esters, preferred hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants

Ionic surfactants, including cationic, anionic and zwitterionic surfactants, are suitable hydrophilic surfactants for use in embodiments of the present invention. Preferred ionic surfactants include quaternary ammonium salts, fatty acid salts and bile salts. Specifically, preferred ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylester of sodium sulfonsuccinic acid, sodium dioctyl sulfosuccinate, sodium cholate, and sodium taurocholate. These quaternary ammonium salts are preferred additives. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Some of the surfactants described herein are very stable under heating. They survive an ethylene oxide sterilization process. They do not react with drugs such as paclitaxel or rapamycin under the sterilization process. The hydroxyl, ester, amide groups are preferred because they are unlikely to react with drug, while amine and acid groups often do react with paclitaxel or rapamycin during sterilization. Furthermore, surfactant additives improve the integrity and quality of the coating layer, so that particles do not fall off during handling. When the surfactants described herein are formulated with paclitaxel, experimentally it protects drug from premature release during the device delivery process while facilitating rapid release and elution of paclitaxel during a very brief deployment time of 0.2 to 10 minutes at the target site. Drug absorption by tissues at the target site is unexpectedly high experimentally.

Chemical Compounds with One or More Hydroxyl, Amino, Carbonyl, Carboxyl, Acid, Amide or Ester Moieties The chemical compounds with one or more hydroxyl, amino, carbonyl, carboxyl, acid, amide or ester moieties include amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide or ester moieties having a molecular weight less than 5,000-10,000 are preferred in certain embodiments. In other embodiments, molecular weight of the additive with one or more hydroxyl, amino, carbonyl, carboxyl, acid, amide, or ester moieties is preferably less than 1000-5,000, or more preferably less than 750-1,000, or most preferably less than 750. In these embodiments, the molecular weight of the additive is preferred to be less than that of the drug to be delivered. Further, the molecular weight of the additive is preferred to be higher than 80 since molecules with molecular weight less than 80 very easily evaporate and do not stay in the coating of a medical device. Small molecules can diffuse quickly. They can release themselves easily from the delivery balloon, accelerating release of drug, and they can diffuse away from drug when the drug binds tissue of the body lumens.

In certain embodiments, more than four hydroxyl groups are preferred, for example in the case of a high molecular weight additive. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. The hydroxyl group is preferred as the hydrophilic moiety because it is unlikely to react with water insoluble drug, such as paclitaxel or rapamycin. In some embodiments, the chemical compound having more than four hydroxyl groups has a melting point of 120° C. or less. In some embodiments, the chemical compound having more than four hydroxyl groups has three adjacent hydroxyl groups that in stereo configuration are all on one side of the molecule. For example, sorbitol and xylitol have three adjacent hydroxyl groups that in stereoconfiguration are all on one side of the molecule, while galactitol does not. The difference impacts the physical properties of the isomers such as the melting temperature. The stereoconfiguration of the three adjacent hydroxyl groups may enhance drug binding. This will lead to improved compatibility of the water insoluble drug and hydrophilic additive, and improved tissue uptake and absorption of drug.

Some of the chemical compounds with one or more hydroxyl, amine, carbonyl, carboxyl, or ester moieties described herein are very stable under heating. They survive an ethylene oxide sterilization process and do not react with the water insoluble drug paclitaxel or rapamycin during sterilization. L-ascorbic acid and its salt and diethanolamine, on the other hand, do not necessarily survive such a sterilization process, and they react with paclitaxel. A different sterilization method is therefore preferred for L-ascorbic acid and diethanolamine. Hydroxyl, ester, and amide groups are preferred because they are unlikely to react with therapeutic agents such as paclitaxel or rapamycin. Sometimes, amine and acid groups do react with paclitaxel, for example, experimentally, benzoic acid, gentisic acid, diethanolamine, and ascorbic acid were not stable under ethylene oxide sterilization, heating, and aging process and reacted with paclitaxel. When the chemical compounds described herein are formulated with paclitaxel, a top coat layer may be advantageous in order to prevent premature drug loss during the device delivery process before deployment at the target site, since hydrophilic small molecules sometimes release drug too easily. The chemical compounds herein rapidly elute drug off the balloon during deployment at the target site. Surprisingly, even though some drug is lost during transit of the device to the target site when the coating contains these additives, experimentally drug absorption by tissue is unexpectedly high after only 0.2-10 minutes of deployment, for example, with the additive hydroxyl lactones such as ribonic acid lactone and gluconolactone.

Fat-Soluble Vitamins and Salts Thereof

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention.

The following examples of fat-soluble vitamin derivatives and/or sources are also useful as additives: Alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). Folic acid is also of this type, and although it is water-soluble at physiological pH, it can be formulated in the free acid form. Other derivatives of fat-soluble vitamins useful in embodiments of the present invention may easily be obtained via well known chemical reactions with hydrophilic molecules.

Water-Soluble Vitamins and their Amphiphilic Derivatives

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and their Salts

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has solubility in unbuffered water of less than about 4% (40 mg/ml). These include Cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well known in the art hydrophilic molecules may be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins

Oligopeptides and peptides are useful as additives, since hydrophobic and hydrophilic amino acids may be easily coupled and various sequences of amino acids may be tested to maximally facilitate permeation of tissue by drug.

Proteins are also useful as additives in embodiments of the present invention. Serum albumin, for example, is a particularly preferred additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and their Esters and Anhydrides

Examples are acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water soluble and can effectively carry the drugs off the device into the vessel walls.

Other Chemical Compounds with One or More Hydroxyl, Amine, Carbonyl, Carboxyl, or Ester Moieties The additives according to embodiments include amino alcohols, alcohols, amines, acids, amides and hydroxyl acids in both cyclo and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly (ethylene glycol) oligomers, di(propylene glycol), tri (propylene glycol), tetra(propylene glycol), and penta (propylene glycol), poly(propylene glycol) oligomers, a block copolymer of polyethylene glycol and polypropylene glycol, and derivatives and combinations thereof.

Combinations of additives are also useful for purposes of the present invention.

One embodiment comprises the combination or mixture of two additives, for example, a first additive comprising a surfactant and a second additive comprising a chemical compound with one or more hydroxyl, amine, carbonyl, carboxyl, or ester moieties.

The combination or mixture of the surfactant and the small water-soluble molecule (the chemical compounds with one or more hydroxyl, amine, carbonyl, carboxyl, or ester moieties) has advantages. Formulations comprising mixtures of the two additives with water-insoluble drug are in certain cases superior to mixtures including either additive alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, or ester moieties. The surfactant has a relatively high Log P (usually above 0) and the water soluble molecules have low Log P (usually below 0). Some surfactants, when used as additives in embodiments of the present invention, adhere so strongly to the water-insoluble drug and the surface of the medical device that drug is not able to rapidly release from the surface of the medical device at the target site. On the other hand, some of the water-soluble small molecules (with one or more hydroxyl, amine, carbonyl, carboxyl, or ester moieties) adhere so poorly to the medical device that they release drug before it reaches the target site, for example, into serum during the transit of a coated balloon catheter to the site targeted for intervention. Suprisingly, by adjusting the ratio of the concentrations of the small hydrophilic molecule and the surfactant in the formulation, the inventor has found that the coating stability during transit and rapid drug release when inflated and pressed against tissues of the lumen wall at the target site of therapeutic intervention in certain cases is superior to a formulation comprising either additive alone. Furthermore, the miscibility and compatibility of the water-insoluble drug and the highly water-soluble molecules is improved by the presence of the surfactant. The surfactant also improves coating uniformity and integrity by its good adhesion to the drug and the small molecules. The long chain hydrophobic part of the surfactant binds drug tightly while the hydrophilic part of the surfactant binds the water-soluble small molecules.

The surfactants in the mixture or the combination include all of the surfactants described herein for use in embodiments of the invention. The surfactant in the mixture may be chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, Tween 80, octoxynol, monoxynol, tyloxapol, sucrose monopalmitate, sucrose monolaurate, decanoyl-N-methylglucamide, n-decyl-.beta.-D-glucopyranoside, n-decyl-.beta.-D-maltopyranoside, n-dodecyl-.beta.-D-glucopyranoside, n-dodecyl-.beta.-D-maltoside, heptanoyl-N-methylglucamide, n-heptyl-.beta.-D-glucopyranoside, n-heptyl-.beta.-D-thioglucoside, n-hexyl-.beta.-D-glucopyranoside, nonanoyl-N-methylglucamide, n-noyl-.beta.-D-glucopyranoside, octanoyl-N-methylglucamide, n-octyl-.beta.-D-glucopyranoside, octyl-.beta.-D-thioglucopyranoside and their derivatives.

The chemical compound with one or more hydroxyl, amine, carbonyl, carboxyl, or ester moieties in the mixture or the combination include all of the chemical compounds with one or more hydroxyl, amine, carbonyl, carboxyl, or ester moieties described herein for use in embodiments of the invention. The chemical compound with one or more hydroxyl, amine, carbonyl, carboxyl, or ester moieties in the mixture has at least one hydroxyl group in one of the embodiments in the inventions. In certain embodiments, more than four hydroxyl groups are preferred, for example in the case of a high molecular weight additive. In some embodiments, the chemical compound having more than four hydroxyl groups has a melting point of 120° C. or less. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. The hydroxyl group is preferred as the hydrophilic moiety because it is unlikely to react with water insoluble drug, such as paclitaxel or rapamycin.

The chemical compound with one or more hydroxyl, amine, carbonyl, carboxyl, or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly (ethylene glycol) oligomers, di(propylene glycol), tri (propylene glycol), tetra(propylene glycol, and penta (propylene glycol), poly(propylene glycol) oligomers, a block copolymer of polyethylene glycol and polypropylene glycol, and derivatives and combinations thereof.

Mixtures or combinations of a surfactant and a water-soluble small molecule confer the advantages of both additives. The water insoluble drug often has a poor compatibility with highly water-soluble chemical compounds, and the surfactant improves compatibility. The surfactant also improves the coating quality, uniformity, and integrity, and particles do not fall off the balloon during handling. The surfactant reduces drug loss during transit to a target site. The water-soluble chemical compound improves the release of drug off the balloon and absorption of the drug in the tissue. Experimentally, the combination was surprisingly effective at preventing drug release during transit and achieving high drug levels in tissue after very brief 0.2-2 minute deployment. Furthermore, in animal studies it effectively reduced stenosis and late lumen loss.

Some of the mixtures or combinations of surfactants and water-soluble small molecules are very stable under heating. They survived an ethylene oxide sterilization process and do not react with the water insoluble drug paclitaxel or rapamycin during sterilization. The hydroxyl, ester, amide groups are preferred because they are unlikely to react with therapeutic agents such as paclitaxel or rapamycin. Sometimes amine and acid groups do react with paclitaxel and are not stable under ethylene oxide sterilization, heating, and aging. When the mixtures or combinations described herein are formulated with paclitaxel, a top coat layer may be advantageous in order to protect the drug layer and from premature drug loss during the device.

Preferred additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, monoxynol, tyloxapol, sucrose monopalmitate, sucrose monolaurate, decanoyl-N-methylglucamide, n-decyl-.beta.-D- glucopyranoside, n-decyl-.beta.-D-maltopyranoside, n-dodecyl-.beta.-D-glucopyranoside, n-dodecyl-.beta.-D-maltoside, heptanoyl-N-methylglucamide, n-heptyl-.beta.-D-glucopyranoside, n-heptyl-.beta.-D-thioglucoside, n-hexyl-.beta.-D-glucopyranoside, nonanoyl-N-methylglucamide, n-noyl-.beta.-D-glucopyranoside, octanoyl-N-methylglucamide, n-octyl-.beta.-D-glucopyranoside, octyl-.beta.-D-thioglucopyranoside; cystine, tyrosine, tryptophan, leucine, isoleucine, phenylalanine, asparagine, aspartic acid, glutamic acid, and methionine (amino acids); cetotiamine; cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof. (chemical compounds with one or more hydroxyl, amino, carbonyl, carboxyl, or ester moieties). Some of these additives are both water-soluble and organic solvent-soluble. They have good adhesive properties and adhere to the surface of polyamide medical devices, such as balloon catheters. They may therefore be used in the adherent layer, top layer, and/or in the drug layer of embodiments of the present invention. The aromatic and aliphatic groups increase the solubility of water insoluble drugs in the coating solution, and the polar groups of alcohols and acids accelerate drug permeation of tissue.

Other preferred additives according to embodiments of the invention include the combination or mixture or amide reaction products of an amino alcohol and an organic acid. Examples are lysine/glutamic acid, lysine acetate, lactobionic acid/meglumine, lactobionic acid/tromethanemine, lactobionic acid/diethanolamine, lactic acid/meglumine, lactic acid/tromethanemine, lactic acid/diethanolamine, gentisic acid/meglumine, gentisic acid/tromethanemine, gensitic acid/diethanolamine, vanillic acid/meglumine, vanillic acid/tromethanemine, vanillic acid/diethanolamine, benzoic acid/meglumine, benzoic acid/tromethanemine, benzoic acid/diethanolamine, acetic acid/meglumine, acetic acid/tromethanemine, and acetic acid/diethanolamine.

Other preferred additives according to embodiments of the invention include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

Other preferred additives that may be useful in embodiments of the present invention include riboflavin, riboflavin-phosphate sodium, Vitamin D3, folic acid (vitamin B9), vitamin 12, diethylenetriaminepentaacetic acid dianhydride, ethylenediaminetetraacetic dianhydride, maleic acid and anhydride, succinic acid and anhydride, diglycolic anhydride, glutaric anhydride, L-ascorbic acid, thiamine, nicotinamide, nicotinic acid, 2-pyrrolidone-5-carboxylic acid, cystine, tyrosine, tryptophan, leucine, isoleucine, phenylalanine, asparagine, aspartic acid, glutamic acid, and methionine.

From a structural point of view, these additives share structural similarities and are compatible with water insoluble drugs (such as paclitaxel and rapamycin). They often contain double bonds such as C=C, C=N, C=O in aromatic or aliphatic structures. These additives also contain amine, alcohol, ester, amide, anhydride, carboxylic acid, and/or hydroxyl groups. They may form hydrogen bonds and/or van der Waals interactions with drug. They are also useful in the top layer in the coating. Compounds containing one or more hydroxyl, carboxyl, or amine groups, for example, are especially useful as additives since they facilitate drug release from the device surface and easily displace water next to the polar head groups and surface proteins of cell membranes and may thereby remove this barrier to hydrophobic drug permeability. They accelerate movement of a hydrophobic drug off the balloon to the lipid layer of cell membranes and tissues for which it has very high affinity. They may also carry or accelerate the movement of drug off the balloon into more aqueous environments such as the interstitial space, for example, of nonvascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic C=N groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for the vessel wall and can displace hydrogen-bound water molecules. At the same time, they have long chains of fatty acid, alcohol, ether and ester that can both complex with hydrophobic drug and integrate into the lipid structure of the cell membranes to form the part of the lipid structure. This deformation or loosening of the lipid membrane of target cells may further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They also have structural components including aromatic C=N, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore preferably used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In embodiments of the present invention, the additive is soluble in aqueous solvents and is soluble in organic solvents. Extremely hydrophobic compounds that lack sufficient hydrophilic parts and are insoluble in aqueous solvent, such as the dye Sudan Red, are not useful as additives in these embodiments. Sudan red is also genotoxic.

In one embodiment, the concentration density of the at least one therapeutic agent applied to the surface of the medical device is from about 1 to 20 $\mu g/mm^2$, or more preferably from about 2 to 6 $\mu g/mm^2$. In one embodiment, the concentration of the at least one additive applied to the surface of the medical device is from about 1 to 20 $\mu g/mm^2$. The ratio of additives to drug by weight in the coating layer in embodiments of the present invention is about 20 to 0.05, preferably about 10 to 0.5, or more preferably about 5 to 0.8.

The relative amount of the therapeutic agent and the additive in the coating layer may vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's octonol-water partition coefficient (P), the melting point of the additive, the water solubility of the additive and/or therapeutic agent, the surface tension of water solutions of the surface modifier, etc.

Other considerations will further inform the choice of specific proportions of different additives. These considerations include the degree of bioacceptability of the additives and the desired dosage of hydrophobic therapeutic agent to be provided.

Therapeutic Agent

The drugs or biologically active materials, which can be used in embodiments of the present invention, can be any therapeutic agent or substance. The drugs can be of various physical states, e.g., molecular distribution, crystal forms or cluster forms. Examples of drugs that are especially useful in embodiments of the present invention are lipophilic substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present invention include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Some drugs that are considered particularly suitable for the airway, sinus and other nasal lumens are corticosteroids such as, budesonide, flunisolide, triamcinolone, beclomethasone, fluticasone, mometasone, mometasone furoate, dexamethasone, hydrocortisone, methylprednisolone, prednisone, cotisone, betamethasone, triamcinolone acetonide, or the like. Some other suitable drugs are bronchodilators such as terbutaline, albuterol, ipratropium, pirbuterol, epinephrine, salmeterol, levalbuterol, formoterol, or the like.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Antioxidant agents can include probucol. Anti-proliferative agents can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, .beta.-sitosterin, ademetionine, myrtecaine, polidocanol, non ivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavonei A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-All, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

Adherent Layer

The adherent layer, which is an optional layer underlying the drug coating layer, improves the adherence of the drug coating layer to the exterior surface of the medical device and protects coating integrity. If drug and additive differ in their adherence to the medical device, the adherent layer may prevent differential loss (during transit) or elution (at the target site) of drug layer components in order to maintain consistent drug-to-additive or drug-to-drug ratio in the drug layer and therapeutic delivery at the target site of intervention. Furthermore, the adherent layer may function to facilitate release of coating layer components which otherwise might adhere too strongly to the device for elution during brief contact with tissues at the target site. For example, in the case where a particular drug binds the medical device tightly, more hydrophilic components are incorporated into the adherent layer in order to decrease affinity of the drug to the device surface.

As described above, the adherent layer comprises a polymer or an additive or mixtures of both. The polymers that are useful for forming the adherent layer are ones that are biocompatible and avoid irritation of body tissue. Some examples of polymers that are useful for forming the adherent layer are polymers that are biostable, such as polyurethanes, silicones, and polyesters. Other polymers that are useful for forming the adherent layer include polymers that can be dissolved and polymerized on the medical device.

Some examples of polymers that are useful in the adherent layer of embodiments of the present invention include polyolefins, polyisobutylene, ethylene-1-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, and mixtures and block copolymers thereof.

Since the medical device undergoes mechanical manipulation, i.e., expansion and contraction, examples of polymers that are useful in the adherent layer include elastomeric polymers, such as silicones (e.g., polysiloxanes and substituted polysiloxanes), polyurethanes, thermoplastic elastomers, ethylene vinyl acetate copolymers, polyolefin elastomers, and EPDM rubbers. Due to the elastic nature of these polymers, when these polymers are used, the coating better adheres to the surface of the medical device when the device is subjected to forces or stress.

The adherent layer may also comprise one or more of the additives previously described, or other components, in order to maintain the integrity and adherence of the coating layer to the device and to facilitate both adherence of drug and additive components during transit and rapid elution during deployment at the site of therapeutic intervention.

Top Layer

In order to further protect the integrity of the drug layer, an optional top layer may be applied to prevent loss of drug during transit through tortuous anatomy to the target site or during the initial expansion of the device before the coating makes direct contact with target tissue. The top layer may release slowly in the body lumen while protecting the drug layer. The top layer will erode more slowly if it is comprised of more hydrophobic, high molecular weight additives. Surfactants are examples of more hydrophobic structures with long fatty chains, such as Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with drug or with the coating layer, such as p-isononylphenoxypolyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-.beta.-D-glucopyranoside, n-decyl-.beta.-D-maltopyranoside, n-dodecyl-.beta.-D-glucopyranoside, n-dodecyl-.beta.-D-maltoside, heptanoyl-N-methylglucamide, n-heptyl-.beta.-D-glucopyranoside, n-heptyl-.beta.-D-thioglucoside, n-hexyl-.beta.-D-glucopyranoside, nonanoyl-N-methylglucamide, n-noyl-.beta.-D-glucopyranoside, octanoyl-N-methylglucamide, n-octyl-.beta.-D-glucopyranoside, octyl-.beta.-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

Solvents

Solvents for preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran. A preferred solvent in the top coating layer is methanol, ethanol, and acetone.

Organic solvents, such as short-chained alcohol, dioxane, tetrahydrofuran, dimethylformamide, acetonitrile, dimethylsulfoxide, etc., are particularly useful and preferred solvents in embodiments of the present invention because these organic solvents generally disrupt collodial aggregates and co-solubilize all the components in the coating solution.

The therapeutic agent and additive or additives may be dispersed in, solubilized, or otherwise mixed in the solvent. The weight percent of drug and additives in the solvent may be in the range of 0.1-80% by weight, preferably 2-20% by weight.

Another embodiment of the invention relates to a method for preparing a medical device, particularly, for example, a balloon catheter or a stent. First, a coating solution or suspension comprising at least one solvent, at least one therapeutic agent, and at least one additive is prepared. In at least one embodiment, the coating solution or suspension includes only these three components. The content of the therapeutic agent in the coating solution can be from 0.5-50% by weight based on the total weight of the solution. The content of the additive in the coating solution can be from 1-45% by weight, 1 to 40% by weight, or from 1-15% by weight based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives may be used in the coating solution.

In other embodiments, a therapeutic agent, an additive and a polymeric material may be used in the coating solution, for example in a stent coating. In the coating, the therapeutic agent is not encapsulated in polymer particles.

Various techniques may be used for applying a coating solution to a medical device such as casting, spinning, spraying, dipping (immersing), ink jet printing, electrostatic techniques, and combinations of these processes. Choosing an application technique principally depends on the viscosity and surface tension of the solution. In embodiments of the present invention, dipping and spraying are preferred because it makes it easier to control the uniformity of the thickness of the coating layer as well as the concentration of the therapeutic agent applied to the medical device. Regardless of whether the coating is applied by spraying or by dipping or by another method or combination of methods, each layer is usually deposited on the medical device in multiple application steps in order to control the uniformity and the amount of therapeutic substance and additive applied to the medical device.

Each applied layer is from about 0.1 microns to 15 microns in thickness. The total number of layers applied to the medical device is in a range of from about 2 to 50. The total thickness of the coating is from about 2 to 200 microns.

As discussed above, spraying and dipping are particularly useful coating techniques for use in embodiments of the present invention. In a spraying technique, a coating solution or suspension of an embodiment of the present invention is prepared and then transferred to an application device for applying the coating solution or suspension to a balloon catheter.

With the balloon rotating in a substantially horizontal plane, the spray nozzle is adjusted so that the distance from the nozzle to the balloon is about 1-4 inches. First, the coating solution is sprayed substantially horizontally with the brush being directed along the balloon from the distal end of the balloon to the proximal end and then from the proximal end to the distal end in a sweeping motion at a speed such that one spray cycle occurred in about three balloon rotations. The balloon is repeatedly sprayed with the coating solution, followed by drying, until an effective amount of the drug is deposited on the balloon.

In one embodiment of the present invention, the balloon is inflated or partially inflated, the coating solution is applied to the inflated balloon, for example by spraying, and then the balloon is deflated and folded before drying. Drying may be performed under vacuum.

It should be understood that this description of an application device, fixture, and spraying technique is exemplary only. Any other suitable spraying or other technique may be used for coating the medical device, particularly for coating the balloon of a balloon catheter or stent delivery system or stent.

After the medical device is sprayed with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C. or higher for approximately 24 hours. Any other suitable method of drying the coating solution may be used. The time and temperature may vary with particular additives and therapeutic agents.

Optional Post Treatment

After depositing the drug-additive containing layer on the device of certain embodiments of the present invention, dimethyl sulfoxide (DMSO) or other solvent may be applied, by dip or spray or other method, to the finished surface of the coating. DMSO readily dissolves drugs and easily penetrates membranes and may enhance tissue absorption.

It is contemplated that the medical devices of embodiments of the present invention have applicability for treating blockages and occlusions of any body lumens, including, among others, the gastrointestinal tract, including the esophagus, stomach, small intestine, and colon, the pulmonary airways, including the trachea, bronchi, bronchioles, the sinus, the biliary tract, the urinary tract, urethral, ureteral, and prostate and other lumens. They are especially suited for treating tissue of the urological tract with, for example, a balloon catheter or a stent.

Yet another embodiment of the present invention relates to a method of treating a prostate. The method includes inserting a medical device comprising a coating into a prostate. The coating layer comprises a therapeutic agent and an additive. In this embodiment, the medical device can be configured as having at least an expandable portion. Some examples of such devices include balloon catheters, perfusion balloon catheters, an infusion catheter such as distal perforated drug infusion catheters, a perforated balloon, spaced double balloon, porous balloon, and weeping balloon, cutting balloon catheters, scoring balloon catheters, self-expanded and balloon expanded-stents, guide catheters, guide wires, embolic protection devices, and various imaging devices.

As mentioned above, one example of a medical device that is particularly useful in the present invention is a coated balloon catheter. A balloon catheter typically has a long, narrow, hollow tube tabbed with a miniature, deflated balloon. In embodiments of the present invention, the balloon is coated with a drug solution. Then, the balloon is maneuvered through the body lumen strictures to the site of a blockage, occlusion, or other tissue requiring a therapeutic agent. Once in the proper position, the balloon is inflated and contacts the walls of the body lumen strictures and/or a blockage or occlusion. It is an object of embodiments of the present invention to rapidly deliver drug to and facilitate absorption by target tissue. It is advantageous to efficiently deliver drug to tissue in as brief a period of time as possible while the device is deployed at the target site. The therapeutic agent is released into such tissue, for example the lumen walls, in about 0.1 to 30 minutes, for example, or preferably about 0.1 to 10 minutes, or more preferably about 0.2 to 2 minutes, or most preferably, about 0.1 to 1 minutes, of balloon inflation time pressing the drug coating into contact with diseased nonvascular tissue.

Given that a therapeutically effective amount of the drug can be delivered by embodiments of the present invention into, for example, the prostate, in some cases the need for a stent may be eliminated, obviating the complications of fracture and dripping associated therewith.

Should placement of a stent still be desired, a particularly preferred use for embodiments of the present invention is to crimp a stent, such as a bare metal stent (BMS), for example, over the drug coated balloon described in embodiments herein. When the balloon is inflated to deploy the stent at the site of diseased nonvasculature, an effective amount of drug is delivered into the arterial wall to prevent or decrease the severity of restenosis or other complications. Alternatively, the stent and balloon may be coated together, or the stent may be coated and then crimped on a balloon.

Further, the balloon catheter may be used to treat non-vascular tissue/disease alone or in combination with other methods for treating the non vasculature, for example, photodynamic therapy or atherectomy. Atherectomy is a procedure to remove plaque from arteries. Specifically, atherectomy removes plaque from peripheral and coronary arteries. The medical device used for peripheral or coronary atherectomy may be a laser catheter or a rotablator or a direct atherectomy device on the end of a catheter. The catheter is inserted into the body and advanced through a nonvascular lumen to the area of narrowing. After the atherectomy has removed some of the plaque, balloon angioplasty using the coated balloon of embodiments of the present invention may be performed. In addition, stenting may be performed thereafter, or simultaneously with expansion of the coated balloon as described above. Photodynamic therapy is a procedure where light or irradiated energy is used to kill target cells in a patient. A light-activated photosensitizing drug may be delivered to specific areas of tissue by embodiments of the present invention. A targeted light or radiation source selectively activates the drug to produce a cytotoxic response and mediate a therapeutic anti-proliferative effect.

In some of the embodiments of drug-containing coatings and layers according to the present invention, the coating or layer does not include polymers, oils, or lipids. And, furthermore, the therapeutic agent is not encapsulated in polymer particles, micelles, or liposomes. As described above, such formulations have significant disadvantages and can inhibit the intended efficient, rapid release and tissue penetration of the agent, especially in the environment of diseased tissue of the nonvasculature.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term "about." Accordingly, unless otherwise indicated to the contrary, the numerical parameters set forth in this specification and attached claims are approximations that may vary depending upon the desired properties sought to be obtained by the present disclosure.

Preparation

The medical device and the coating layers of embodiments of the present invention can be made according to various methods. For example, the coating solution can be prepared by dispersing, dissolving, diffusing, or otherwise mixing all the ingredients, such as a therapeutic agent, an additive, and a solvent, simultaneously together. Also, the coating solution can be prepared by sequentially adding each component based on solubility or any other parameters. For example, the coating solution can be prepared by first adding the therapeutic agent to the solvent and then adding the additive. Alternatively, the additive can be added to the solvent first and then the therapeutic agent can be later added. If the solvent used does not sufficiently dissolve the drug, it is preferable to first add the additive to the solvent, then the drug, since the additive will increase drug solubility in the solvent.

EXAMPLES

The following examples include embodiments of medical devices and coating layers within the scope of the present invention. While the following examples are considered to embody the present invention, the examples should not be interpreted as limitations upon the present invention.

Example 1

Preparation of Coating Solutions

Formulation 1—50-150 mg (0.06-0.18 mmole) paclitaxel, 2-6 ml acetone (or ethanol), 25-100 mg ascorbyl palmitate, 25-100 mg L-ascorbic acid and 0.5 ml ethanol were mixed.

Formulation 2—50-150 mg (0.05-0.16 mmole) rapamycin, 2-6 ml acetone (or ethanol), 50-200 mg polyglyceryl-10 oleate and 0.5 ml ethanol were mixed.

Formulation 3—50-150 mg (0.06-0.18 mmole) paclitaxel, 2-6 ml acetone (or ethanol), 50-200 mg octoxynol-9 and 0.5 ml ethanol were mixed.

Formulation 4—50-150 mg (0.05-0.16 mmole) rapamycin, 2-6 ml acetone (or ethanol), 50-200 mg p-isononylphenoxypolyglycidol and 0.5 ml ethanol were mixed.

Formulation 5—50-150 mg (0.06-0.18 mmole) paclitaxel, 2-6 ml acetone (or ethanol), 50-200 mg Tyloxapol and 0.5 ml ethanol were mixed.

Formulation 6—50-150 mg (0.05-0.16 mmole) rapamycin in 2-6 ml acetone (or ethanol), 50-150 mg L-ascorbic acid in 1 ml water or ethanol, both, then were mixed.

Formulation 7—50-150 mg (0.06-0.18 mmole) paclitaxel, 2-6 ml acetone (or ethanol), 50-150 mg niacinamide in 1 ml water or ethanol, were mixed.

Formulation 8—50-150 mg (0.05-0.16 mmole) rapamycin, 2-6 ml acetone (or ethanol), 50-200 mg nicotinic acid in 1 ml water or ethanol, were mixed.

Formulation 9—50-150 mg (0.06-0.18 mmole) paclitaxel, 2-6 ml ethanol (or acetone), 150 mg thiamine hydrochloride in 1 ml water, and 0.5 ml were mixed.

Formulation 10—50-150 mg (0.05-0.16 mmole) rapamycin, 2-6 ml acetone or ethanol, 150 mg 2-pyrrolidone-5-carboxylic acid in 1 ml water or ethanol, were mixed.

Formulation 11—50-150 mg (0.06-0.18 mmole) paclitaxel, 2-6 ml acetone (or ethanol), 75 mg p-isononylphenoxypolyglycidol, 75 mg niacinamide in 1 ml water or ethanol, and 0.5 ml ethanol were mixed.

Formulation 12—50-150 mg (0.05-0.16 mmole) rapamycin, 2-6 ml acetone (or ethanol), 75 mg Octoxynol-9, 75 mg thiamine hydrochloride in 1 ml water or ethanol, and 0.5 ml ethanol were mixed.

Formulation 13—50-150 mg (0.06-0.18 mmole) paclitaxel, 2-6 ml acetone (or ethanol), 75 mg p-isononylphenoxypolyglycidol, 75 mg 2-pyrrolidone-5-carboxylic acid in 1 ml water or ethanol, and 0.5 ml ethanol were mixed.

Formulation 14—50-150 mg (0.06-0.18 mmole) paclitaxel, 2-6 ml acetone (or ethanol), 75 mg p-isononylphenoxypolyglycidol, 75 mg nicotinic acid in 1 ml water or ethanol, and 0.5 ml ethanol were mixed.

Formulation 15 50-150 mg (0.06-0.18 mmole) paclitaxel, 2-6 ml acetone (or ethanol), 75 mg p-isononylphenoxypolyglycidol, 75 mg L-ascorbic acid in 1 ml water or ethanol, and 0.5 ml ethanol were mixed.

Formulation 16 50-150 mg (0.06-0.18 mmole) paclitaxel was dissolved in 5-10 ml methylene chloride. The solution was added to 30 ml of human serum albumin solution (5% w/v). The solution was then homogenized for 5 minutes at low speed to form an emulsion. The emulsion was then sonicated at 40 kHz at 50-90% power at 0 to 5° C. for 1 to 5 min.

Formulation 17—50-150 mg (0.05-0.16 mmole) rapamycin was dissolved in 5-10 ml methylene chloride and 10-30 mg p-isononylphenoxypolyglycidol. The solution was added to 30 ml of human serum albumin solution (5% w/v). The solution was then homogenized for 5 minutes at low speed to form an emulsion. The emulsion was then sonicated at 40 kHz at 50-90% power at 0 to 5° C. for 1 to 5 min.

Formulation 18—50-100 mg (0.06-0.12 mmole) paclitaxel, 1-1.6 ml acetone, 1-1.6 ml ethanol, 0.4-1.0 ml water, and 50-200 mg gluconolactone were mixed.

Formulation 19—35-70 mg (0.042-0.084 mmole) paclitaxel, 0.5-1.0 ml acetone, 0.5-1.0 ml ethanol, 35-70 mg Tween 20, and 35-70 mg N-octanoyl N-methylglucamine were mixed.

Formulation 20—35-70 mg (0.042-0.084 mmole) paclitaxel, 0.4-1.0 ml acetone, 0.4-1.0 ml ethanol, 0.2-0.4 ml water, 35-70 mg Tween 20, and 35-70 mg sorbitol were mixed.

Formulation 21—40-80 mg (0.048-0.096 mmole) paclitaxel, 0.5-1.0 ml acetone, 0.5-1.0 ml ethanol, 40-80 mg meglumine, and 32-64 mg gensitic acid (equal molar ratio with meglumine) were mixed.

Formulation 22—35-70 mg (0.042-0.084 mmole) paclitaxel, 0.4-0.8 ml acetone, 0.4-0.8 ml ethanol, 0.25-0.50 ml water, 35-70 mg lactobionic acid, and 10-20 mg diethanolamine (equal molar ratio with lactobionic acid) were mixed.

Formulation 23—35-70 mg (0.042-0.084 mmole) paclitaxel, 0.5-1.0 ml acetone, 0.5-1.0 ml ethanol, and 70-140 mg N-octanoyl N-methylglucamine were mixed.

Formulation 24—35-70 mg (0.042-0.084 mmole) paclitaxel, 0.4-0.8 ml acetone, 0.4-0.8 ml ethanol, 0.2-0.4 ml water, 35-70 mg meglumine, and 18-36 mg lactic acid (equal molar ratio with meglumine) were mixed.

Formulation 25—50-100 mg (0.06-0.12 mmole) paclitaxel, 0.8-1.6 ml acetone, 0.8-1.6 ml ethanol, 0.4-1.0 ml water, 50-100 mg gensitic acid, and 30-60 mg diethanolamine (equal molar ratio with gensitic acid) were mixed.

Formulation 26—Comparison solution-50 mg (0.06 mmole) paclitaxel, 1 ml ethanol, 0.2 ml acetone, 0.042 ml Ultravist 370 were mixed.

Formulation 27—Comparison solution-40 mg (0.048 mmole) paclitaxel, 0.5 ml ethanol, 0.5 ml acetone were mixed.

Formulation 28—35-70 mg (0.042-0.084 mmole) paclitaxel, 0.5-1.0 ml acetone, 0.5-1.0 ml ethanol, 35-70 mg Triton X-100, and 35-70 mg N-heptanoyl N-methylglucamine were mixed.

Example 2

5 PTA balloon catheters (4-8 mm in diameter and 20 mm in length) were folded with three wings under vacuum. The folded balloon under vacuum was sprayed or dipped in a formulation (1-28) in example 1. The folded balloon was then dried, sprayed or dipped again, dried again, and sprayed or dipped again until sufficient amount of drug on the balloon (3 microgram per square mm) was obtained. The coated folded balloon was then rewrapped and sterilized for animal testing.

Example 3

5 PTA balloon catheters (4-8 mm in diameter and 20 mm in length) were folded with three wings under vacuum. The folded balloon under vacuum was sprayed or dipped in a formulation (1-28) in example 1. The folded balloon was then dried, sprayed or dipped again in a formulation (6-10), dried, and sprayed or dipped again until sufficient amount of drug on the balloon (3 microgram per square mm) was obtained. The coated folded balloon was then rewrapped and sterilized for animal testing.

Example 4

5 PTA balloon catheters crimped with bare metal stent (4-8 mm in diameter and 20 mm in length) were sprayed or dipped in a formulation (1-28) in example 1. The stent delivery system was then dried, sprayed or dipped again in a formulation (20-28), dried and sprayed or dipped again until sufficient amount of drug on the stent and balloon (3 microgram per square mm) is obtained. The coated folded stent delivery system was then sterilized for animal testing.

Example 5

Drug coated balloon catheters and uncoated balloon catheters (as control) were inserted into prostate in pigs. The balloon was over dilated (1:1.2), and the inflated balloon was held in the vessel for 60 seconds to release drug and additive, then deflated and withdraw from the pig. The animals were angiographed after 3 days, 31 days, 3 months, 6 months, 9 months and 12 months. The amount of drug in the artery tissues of the sacrificed animal was measured after 60 minutes, 3 days, 31 days, 3 months, 6 months, 9 months and 12 months.

Example 6

5 stents (3 mm in diameter and 18 mm in length) were spray or dip coated with the formulation (1-28) in example 1. The stents were then dried, sprayed or dipped again, and dried again until a sufficient amount of drug on the stent (3 microgram per square mm) is obtained. The coated stent was then crimped on PTA balloon catheters (3-8 mm in diameters and 20 mm in length). The coated stents with balloon catheters were then sterilized for animal testing.

Example 7

The drug coated stent and uncoated stent (as control) were inserted into urological tract in dogs, then the balloon was over dilated (1:1.2). The stent was implanted and drug and additive released, and the balloon was deflated and withdrawn from the pig. The animals were then angiographed after 5, 30, 60 minutes, 3 days, 31 days, 3 months, 6 months, 9 months and 12 months. The amount of drug in the artery tissues of the sacrificed animal was measured 60 minutes, 1 day, 3 days, 31 days, 3 months, 6 months, 9 months and 12 months.

Example 8

5 PTA balloon catheters were sprayed or dipped in the formulation (1-17) in example 1, dried, and sprayed or dipped and dried again until sufficient amount of drug on balloon is obtained (3 microgram per square mm) was obtained. A bare metal coronary stent (3-6 mm in diameter and 20 mm in length) was crimped on each coated balloon. The coated balloons with crimped bare metal stents were then wrapped and sterilized for animal test.

Example 9

5 PTCA balloon catheters were sprayed or dipped in a formulation (1-5) in example 1, dried, and sprayed or dipped again in a formulation (6-10). Balloons were then dried and sprayed or dipped again until sufficient amount of drug on the balloon (3 microgram per square mm) was obtained. A bare metal coronary stent (3 mm in diameter and 20 mm in length) was crimped on each coated balloon. The coated balloons with crimped bare metal stents were then wrapped and sterilized for animal test.

Example 10

The drug coated balloon-expandable bare metal stent of Examples 8 and 9 and plain balloon-expandable bare metal stent (as control) were inserted into urethral in dogs, and the balloon is over dilated (1:1.2). Stent is implanted, and the balloon was held inflated for 60 seconds to release drug and additive, and the balloon was deflated and withdrawn from the pig. The animals were then angiographed after 5, 30, 60 minutes, 3 days, 31 days, 3 months, 6 months, 9 months and 12 months. The amount of drug in the artery tissues of the sacrificed animal is measured after 60 minutes, 1 day, 3 days, 31 days, 3 months, 6 months, 9 months and 12 months.

Example 11

150 mg (0.18 mmole) paclitaxel, 5 ml acetone (or ethylacetate or methyl ethyl ketone), 150 mg acetic anhydride or maleic anhydride or diglycolic anhydride and 0.5 ml ethanol were mixed, then stirred until a solution was obtained. 5 PTCA balloon catheters were sprayed or dipped in the solution, dried, and sprayed or dipped again until sufficient amount of drug on the balloon (3 microgram per square mm) is obtained. The coated balloon was then treated under high pH (range pH 8-11.5) conditions to hydrolyze the anhydride. This can be confirmed by IR method. The hydrophilicity of the coating was now increased. The coated balloons were then sterilized for animal test.

Example 12

The drug coated balloon catheters and uncoated balloon catheters (as control) were inserted via a bronchoscope into the pulmonary airway in pigs. The balloon was dilated, and the inflated balloon was held expanded in the lumen for 60 seconds to release drug and additive. The balloon was deflated and withdrawn from the pig. The animals were then examined bronchoscopically and tissues samples were taken for pathology and quantification of drug uptake after 3 days, 31 days, 3 months, 6 months, 9 months and 12 months.

Example 13

The uncoated stent delivery catheters were inserted into the esophageal lumen in pigs. The balloon was dilated, the stent was deployed and the deflated balloon was the withdrawn. The pharmaceutical formulation 1-15 of example 1 (10-100 ml) was injected (about 5-15 mg drug per pig) at the site of stent implantation. The drug was then absorbed by injured tissue. The animals were then examined and tissues samples were taken for pathology.

Example 14

The diseased tissue (breast cancer or prostate or atheroma or stenosis) was removed surgically from a human body. The pharmaceutical formulation 1-28 of example 1 (10-100 ml) was then injected into or onto the surgical cavities created by the surgical intervention (about 5-20 mg drug). The local drug delivery included injection by long needle, guide catheters, introducer shealth, drug infusion tube and other drug delivery catheters. The drug was then absorbed by tissue at the target site.

Example 15

6 PTCA balloon catheters (3.5 and 3.0 mm in diameter and 20 mm in length) were inflated at 1-3 atm. The inflated balloon was loaded with a formulation 18-28 in example 1. A sufficient amount of drug on the balloon (3 microgram per square mm) was obtained. The inflated balloon was folded, and then dried. The coated folded balloon was then rewrapped and sterilized for animal testing.

The coated PTA balloon catheter was inserted into a target site in the prostate or urethral of a 25-45 pound dogs. The balloon was inflated to about 12 atm. The overstretch ratio (the ratio of balloon diameter to vessel diameter) was about 1.15-1.20. The drug delivered into the target tissue during 30-60 seconds of inflation. The balloon catheter was then deflated and was withdrawn from animal body. The target prostate was harvested 0.25-24 hours after the procedure. The drug content in the target tissue and the residual drug remaining on the balloon were analyzed by tissue extraction and HPLC.

In chronic animal tests, angiography or endoscope was performed before and after all interventions and at 28-35 days after the procedure. Luminal diameters were measured and late lumen loss was calculated. Late lumen loss is the difference between the minimal lumen diameter measured after a period of follow-up time and the minimal lumen diameter measured immediately after the intervention. Restenosis may be quantified by the diameter stenosis, which is the difference between the mean lumen diameters at follow-up and immediately after the procedure divided by the mean lumen diameter immediately after the procedure. The animal test results for Formulations 18-28 are reported below. All data is an average of five or six experimental data points.

The drug content of the formulation 20 on the 3.5-6.5 mm balloon catheters was about 2 μg/mm². After the procedure, the residual drug on the balloon was 2-45% of the total drug loaded on the balloon. The drug content in tissue harvested 15-30 minutes after the procedure was 3-15% of the total drug content originally loaded on the balloon.

The drug content of formulation 20 on the 3.5 mm balloon catheters was 2 g/mm². After the procedure, the residual drug on the balloon was 5-45% of the total drug load. The drug content in tissue harvested 15-30 minutes after the procedure was 3-15% of the total drug load. The stretch ratio was 1.3 in the procedure.

What is claimed is:

1. A method for treating sinusitis, a sinus stricture, or a nasal lumen, the method comprising:
   inserting a balloon catheter into a target site, wherein the target site is the sinus stricture or the nasal lumen, the balloon catheter comprising
   a coating layer overlying an exterior surface of a balloon that is inflatably expandable, the coating layer comprising
      an initial drug load comprising a therapeutic agent chosen from rapamycin, a rapamycin analogue, and a combination thereof, wherein the initial drug load has a density of the therapeutic agent in the coating layer of 1 to 20 µg per mm² of the exterior surface of the balloon, and
      an additive comprising
         a water-soluble first additive that comprises more than one hydroxyl group, wherein the water-soluble first additive has a molecular weight of 50 to 750; and
         a water-soluble second additive that is different than the first water-soluble additive and that comprises more than one hydroxyl group, wherein the water-soluble second additive has a molecular weight of 750 to 1,000;
   inflating the balloon at least until the coating layer contacts walls of the target site to transfer at least some of the coating layer to the walls of the target site, wherein the coating layer contacts the walls of the target site for an inflation period that is from 0.1 minutes to 30 minutes;
   deflating the balloon at completion of the inflation period; and
   withdrawing the balloon catheter from the target site, wherein after the withdrawing of the balloon catheter from the target site the balloon has thereon a residual drug amount that is less than or equal to 45% of the initial drug load, and after the inflation period the walls of the target site comprise an amount of the therapeutic agent that is 0.1% to 25% of the initial drug load.

2. The method of claim 1, wherein after the withdrawing of the balloon catheter from the target site the balloon has thereon a residual drug amount that 2 to 45% of the initial drug load, and wherein after the inflation period the walls of the target site comprise an amount of the therapeutic agent that is 2% to 25% of the initial drug load.

3. The method of claim 1, wherein during the transferring of the coating layer to the walls of the target site, the coating layer makes uniform direct pressure contact with the walls of the target site.

4. The method of claim 1, wherein the additive further comprises an excipient, a natural product or derivative thereof, an oligomer, a surfactant, or a combination thereof.

5. The method of claim 1, wherein the additive further comprises a polysorbate, polyethylene glycol, polypropylene glycol, polyvinyl pyrrolidinone, a glycerol fatty acid ester, a fatty acid, a poloxamer, 2-hydroxypropyl cyclodextrin, sucrose monopalmitate, sucrose monolaurate, glycerol, an alcohol, a propylene glycol fatty acid ester, cellulose, polycaprolactone, a polyester, a polyurethane, a polylactic acid-polyethylene oxide copolymer, or a combination thereof.

6. The method of claim 1, wherein the additive further comprises a polysorbate, polyethylene glycol, polyvinyl pyrrolidinone, a glycerol fatty acid ester, or a combination thereof.

7. The method of claim 1, wherein the additive further comprises polyvinyl pyrrolidone.

8. The method of claim 1, wherein the additive further comprises a polysorbate.

9. The method of claim 8, wherein the polysorbate is a PEG sorbitan fatty ester, a PEG sorbitan monolaurate, a PEG sorbitan monopalmitate, a PEG sorbitan monooleate, a PEG sorbitan monostearate, PEG-20 sorbitan monolaurate, PEG-20 sorbitan monopalmitate, PEG-20 sorbitan monooleate, PEG-20 sorbitan monostearate, or a combination thereof.

10. The method of claim 1, wherein the additive further comprises a glycerol fatty acid ester.

11. The method of claim 1, wherein the additive further comprises a polysorbate and polyethylene glycol.

12. The method of claim 1, wherein a ratio of the additive to the initial drug load in the coating layer by weight is 20:1 to 0.05:1.

13. The method of claim 1, wherein a ratio of the additive to the initial drug load in the coating layer by weight is 10:1 to 0.5:1.

14. The method of claim 1, wherein the ratio of the additive to the initial drug load in the coating layer by weight is 5:1 to 0.8:1.

15. The method of claim 1, wherein the initial drug load has a density of the therapeutic agent in the coating layer of 2 to 10 µg per mm² of the exterior surface of the balloon.

16. The method of claim 1, wherein the initial drug load has a density of the therapeutic agent in the coating layer of 2 to 6 µg per mm² of the exterior surface of the balloon.

17. The method of claim 1, wherein the coating layer has a uniform thickness.

18. The method of claim 1, wherein the balloon has a uniform circular cross-section perpendicular to a longitudinal direction of the balloon.

19. The method of claim 1, wherein the target site is the sinus stricture.

20. The method of claim 1, wherein the method is a method for treating sinusitis.

21. The method of claim 1, wherein the method is a method of treating a nasal lumen, wherein the target site is the nasal lumen.

* * * * *

UNITED STATES PATENT AND TRADEMARK OFFICE
CERTIFICATE OF CORRECTION

PATENT NO. : 10,675,386 B2
APPLICATION NO. : 16/267434
DATED : June 9, 2020
INVENTOR(S) : Lixiao Wang It is certified that error appears in the above-identified patent and that said Letters Patent is hereby corrected as shown below:

On the Title Page

On page 3, in Column 1, under "Other Publications", Line 46, delete "Respone" and insert --Response-- therefor On page 3, in Column 2, under "Other Publications", Lines 49-50, delete "alt uzosin" and insert --alfuzosin-- therefor On page 4, in Column 2, under "Other Publications", Line 21, delete "Respone" and insert --Response-- therefor In the Specification In Column 47, Line 4, delete "g/mm$^2$." and insert --µg/mm$^2$.-- therefor Signed and Sealed this
Eighteenth Day of August, 2020

Andrei Iancu
*Director of the United States Patent and Trademark Office*